United States Patent
Robbins et al.

(10) Patent No.: US 7,767,446 B2
(45) Date of Patent: Aug. 3, 2010

(54) PERFUSION BIOREACTORS FOR CULTURING CELLS

(75) Inventors: Neil F. Robbins, Cary, NC (US); Jon Rowley, Ann Arbor, MI (US); Mark Quinto, Delran, NJ (US); Abel Z. Hastings, Durham, NC (US); Bryan G. Towns, Union Bridge, MD (US); Bradley R. Snodgrass, Watertown, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1356 days.

(21) Appl. No.: 11/227,489

(22) Filed: Sep. 16, 2005

(65) Prior Publication Data

US 2006/0110822 A1 May 25, 2006

Related U.S. Application Data

(60) Provisional application No. 60/714,516, filed on Sep. 16, 2004, provisional application No. 60/699,849, filed on Jul. 18, 2005.

(51) Int. Cl.
C12M 1/14 (2006.01)
C12M 3/04 (2006.01)

(52) U.S. Cl. ............... 435/299.2; 435/289.1; 435/293.1

(58) Field of Classification Search ............... 435/299.2, 435/297.5
See application file for complete search history.

(56) References Cited

U.S. PATENT DOCUMENTS

| 5,081,035 | A | 1/1992 | Halberstadt |
|---|---|---|---|
| 6,121,042 | A | 9/2000 | Peterson |
| 6,197,575 | B1 | 3/2001 | Griffith |
| 6,548,263 | B1 | 4/2003 | Kapur et al. |
| 6,632,651 | B1 | 10/2003 | Nevo |
| 2003/0215941 | A1 | 11/2003 | Campbell et al. |
| 2004/0034434 | A1* | 2/2004 | Evans et al. ............... 623/23.51 |
| 2004/0208761 | A1 | 10/2004 | Bader |
| 2005/0158851 | A1 | 7/2005 | Furey |
| 2005/0186671 | A1 | 8/2005 | Cannon |
| 2005/0260745 | A1 | 11/2005 | Domansky |
| 2005/0287670 | A1 | 12/2005 | Gulliver |
| 2006/0141623 | A1 | 6/2006 | Smith et al. |

FOREIGN PATENT DOCUMENTS

WO WO 03/087292 A2 10/2003

OTHER PUBLICATIONS

International Search Report for PCT/US05/32818, dated Aug. 31, 2006.

* cited by examiner

*Primary Examiner*—William H Beisner
*Assistant Examiner*—Michael Hobbs
(74) *Attorney, Agent, or Firm*—Alston & Bird LLP

(57) ABSTRACT

A bioreactor system comprising a multi-well platform including an array of bioreactor units. The bioreactor system comprises a perfusion unit and a fluid source unit fluidly interconnected by a pumping unit. The perfusion unit comprises a multi-well plate including a plurality of main chambers configured to house or contain a cell culture and in each bioreactor unit an independent cell study or experiment may be performed.

15 Claims, 21 Drawing Sheets

PERFUSION BIOREACTORS FOR CULTURING CELLS

CROSS-REFERENCE TO RELATED APPLICATIONS

The present application claims benefit to U.S. Provisional Patent Application Ser. No. 60/714,516, filed Sep. 16, 2004, and U.S. Provisional Patent Application Ser. No. 60/699,849, filed Jul. 18, 2005, the entire contents of which are incorporated herein.

FIELD OF THE INVENTION

The present invention relates generally to the field of bioreactors, and, more particularly, to a system and method for culturing cells under perfusion flow, in a single chamber or in a high throughput format.

BACKGROUND OF THE INVENTION

Recent developments in cell/tissue engineering have recognized benefits to growing and studying cells in dynamic environments. Spinner flasks, rotary devices, perfusion bioreactors, or fluid sheer chambers have all been used to enhance nutrient and metabolite diffusion to and from cells. The mechanical aspects of fluid sheer forces have also been shown to trigger second messenger signals and alter cellular gene expression. While these new culture conditions have been recognized to affect cell functions (growth, signaling, morphology, differentiation, etc.), devices for studying these environments have not been translated to high throughput platforms. Furthermore, systems that incorporate three-dimensional scaffolds with highly aligned pores for long-range control over fluid flow paths have also not been established.

Fluid flow was first established as a regulator of cellular gene expression in two-dimensional culture systems with flowing culture medium over cells adherent to glass slides. Cells respond to the fluid sheer by aligning in the direction of the force, and altering their gene expression. These two-dimensional devices are now commercially available from, for example, Flex-Cell International, as well as other vendors. Fluid flow studies have recently been translated to three-dimensional scaffolds, and it has been established that fluid sheer is another important factor in maintaining hepatocyte and bone differentiation. The true importance of fluid flow as an environmental signaling factor, however, has not been fully appreciated because it is difficult to screen against or study in conjunction with a plethora of other environmental cues that are known to alter cell function including but not limited to signaling factors such as growth factors, ECMs, cytokines, media factors, and small molecules to name a few. For example, to date, all of the devices designed to study how these forces affect cell cultures are one-pot or single chamber devices. These devices may be utilized to study how rotation or fluid sheer forces affect cells under one condition at a time, but not under different or varying conditions, which greatly limits the utility of these devices. Accordingly, current devices are not suitable for performing medium or high throughput experimentation for optimization of conditions for controllable cell phenotype, or for testing substances such as molecules of unknown function for altering specific functions in highly relevant cell or engineered tissue cultures.

Furthermore, in the field of drug discovery, the use of primary human cells to study ADMETox (ADMETox is an acronym for set of analyses that measure the absorption, distribution, metabolism, elimination and toxicity of a drug candidate) properties of drugs is highly desirable. This is due to the fact that whole animal studies are expensive, and results are not always predictive of responses in man. In vitro study of primary human cells is attractive due to the economics of the approach, and the fact that data from human cells should be more relevant than animal data. Unfortunately, the culture of primary human cells is extremely difficult for most cell types, and there are few model systems that are capable of creating relevant models of in vivo tissues and organs. As an intermediate between whole animals and primary cells, tissue or organ slices offer an alternative that keeps cells in their native setting (not dissociating them from their microenvironment), while allowing for in vitro testing of xenobiotic effects on cell viability, metabolism, and other ADMET-type aspects that one desires. For example, liver slices are often utilized for measuring liver-specific drug toxicity, as well as CYP induction.

In vitro culture of tissue slices also has several challenges. For example, one significant challenge is the high metabolic rates and nutrient requirements that tissue slices need in vitro. Since the tissue slices require a large nutrient load, it is necessary to culture these slices in large quantities of medium. However, the more medium that one adds to a culture increases the diffusion distance of oxygen to the extent that the rate of consumption by the tissue is greater than the diffusion of oxygen, leading to hypoxic conditions and cell death. There is, therefore, a great need for bioreactor-type devices that enhance nutrient and metabolite transport while maintaining a medium-to-high throughput parallel testing format.

A need exists for a system and method for culturing cells under fluid perfusion in medium to high throughput format, to test and/or discover how new environments alter the ability of cells to respond to other chemical or physical cues in the presence of fluid sheer and to facilitate the systematic and high throughput discovery of dynamic cell culture conditions for cell growth and differentiation, and then utilizing these optimized environments for creating in vitro engineered tissues for therapeutic, diagnostic, or research purposes. A need also exists for a perfusion system that allows for the dynamic and multiplexed culture of a variety of tissue or organ slices for ADMET and tissue culture applications.

SUMMARY OF THE INVENTION

The present invention is directed to a bioreactor system including a perfusion unit, a pumping unit in fluid communication with the perfusion unit, and a fluid source unit in fluid communication with the pumping unit. The perfusion unit includes an array of cell wells configured to contain cell cultures and the fluid source unit includes an array of media wells configured to contain cell culture media. The pumping unit includes an array of pumping elements in fluid communication with the cell wells and media wells and is configured to pump cell culture media from the media cells to the cell wells.

In a preferred embodiment, each of said cell wells is adapted and configured to contain a scaffold having a porous structure. In one embodiment, the scaffold is a two-dimensional scaffold. In another embodiment, the scaffold is a three-dimensional scaffold. In one embodiment, the three-dimensional scaffold may include directionally aligned pores.

In one embodiment, the fluid is deliverable directly into the internal structure of said scaffold. In another embodiment, a return pathway is provided for the fluid to flow from the array of cell wells to the array of media wells. In a preferred embodiment, each pathway is in fluid communication with a single cell well and a single media well.

In another embodiment, the perfusion unit is removably couplable to the pumping unit and each pumping element may comprise a fluid stem having a fluid port therein. Each stem may be configured to extend into the cell wells. In another aspect of the invention, each cell well may include a scaffold coupled thereto configured to receive a portion of the stem internal thereto. The fluid source unit is also removably couplable to the pumping unit.

The present invention is also directed to a method of growing cells, comprising pumping cell culture media from a first array of wells of a fluid source unit into a second array of wells of a perfusion unit, wherein each well of the perfusion unit is adapted and configured to house a cell adherent structure. In one embodiment the method further comprises the step of perfusing the media into and through a scaffold. In one embodiment, the cell adherent structure comprises a two-dimensional scaffold, and in another embodiment the cell adherent structure comprises a three-dimensional scaffold. The first array of wells is in fluid communication with the second array of wells for the return of media to the second array of wells. In another method, each well of the first array of wells is in singular fluid communication with a corresponding well of the second array of wells.

The present invention is also directed to a perfusion bioreactor system, including an array of bioreactor units. Each bioreactor unit includes a cell adherent structure in fluid communication with a fluid stored in a fluid reservoir and, in operation, fluid flows from the fluid source directly into and through the cell adherent structure. In one variation, the cell adherent structure is a three-dimensional scaffold having a porous structure, and in another variation the cell adherent structure is a two-dimensional scaffold. In another preferred embodiment, the cell adherent structure is fluidly interconnected to the fluid reservoir by a pumping unit.

DESCRIPTION OF THE PREFERRED EMBODIMENTS

The present invention relates to bioreactors generally, and, more particularly, to a system and method for culturing cell specimens under perfusion flow, in a single chamber or in a high throughput format for the high throughput discovery of complex environments for controlling cell function and engineered tissue development. The present invention may also be utilized for creating highly relevant cell cultures and systems for direct drug testing on cells in dynamic cell cultures, for drug discovery, drug testing, or ADMETox applications.

Figure 1:
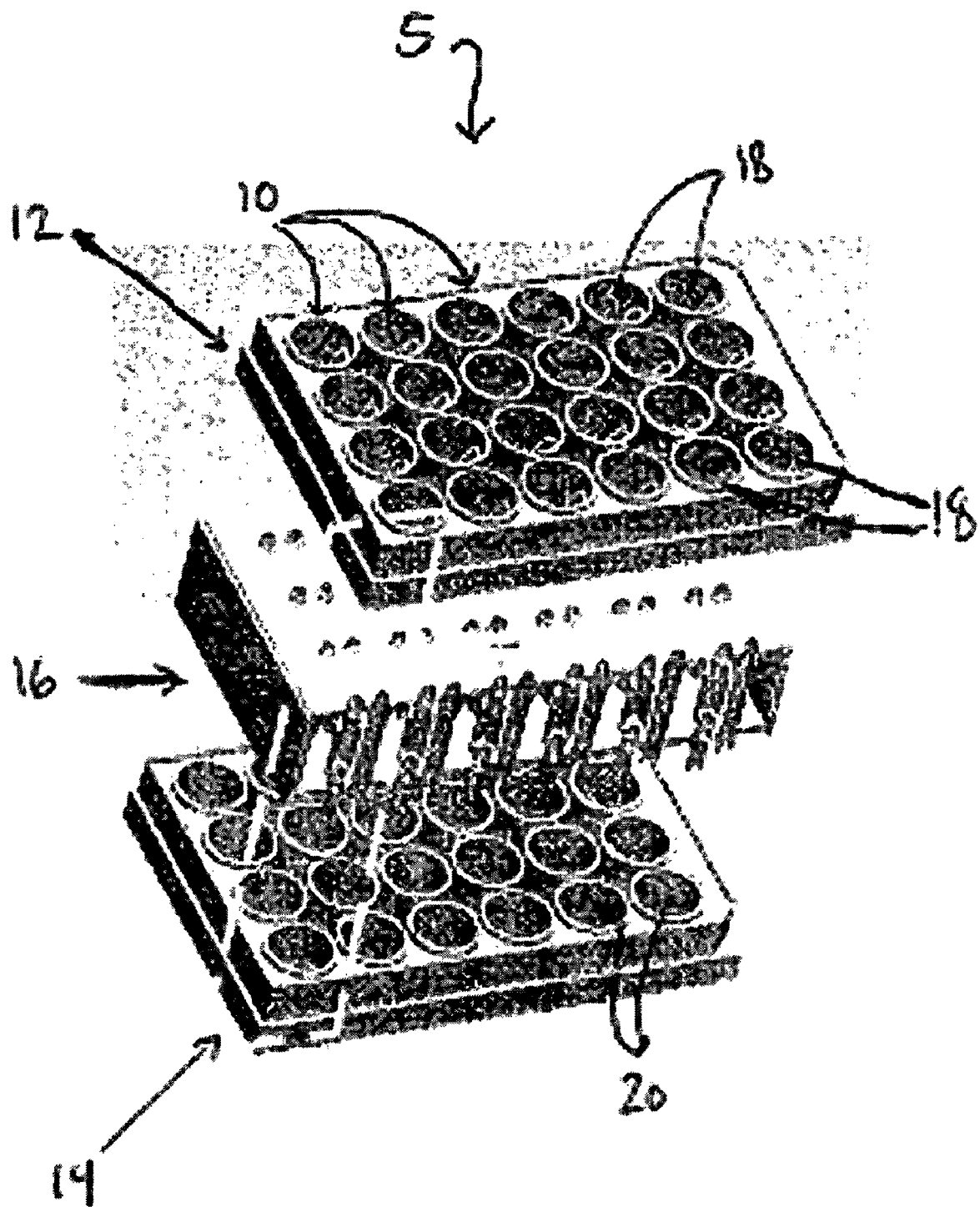
FIG. 1 is an exploded view of a first embodiment of a bioreactor system according to the present invention.

Referring to FIG. 1, a preferred embodiment of a bioreactor system 5 generally includes a multi-well platform comprising an array of bioreactor units 10 wherein in each bioreactor unit, an independent cell study or experiment may be performed. As shown in FIG. 1, the bioreactor system 5 comprises a perfusion unit 12 and a fluid source unit 14 fluidly interconnected by a pumping unit or station 16.

Figure 2:
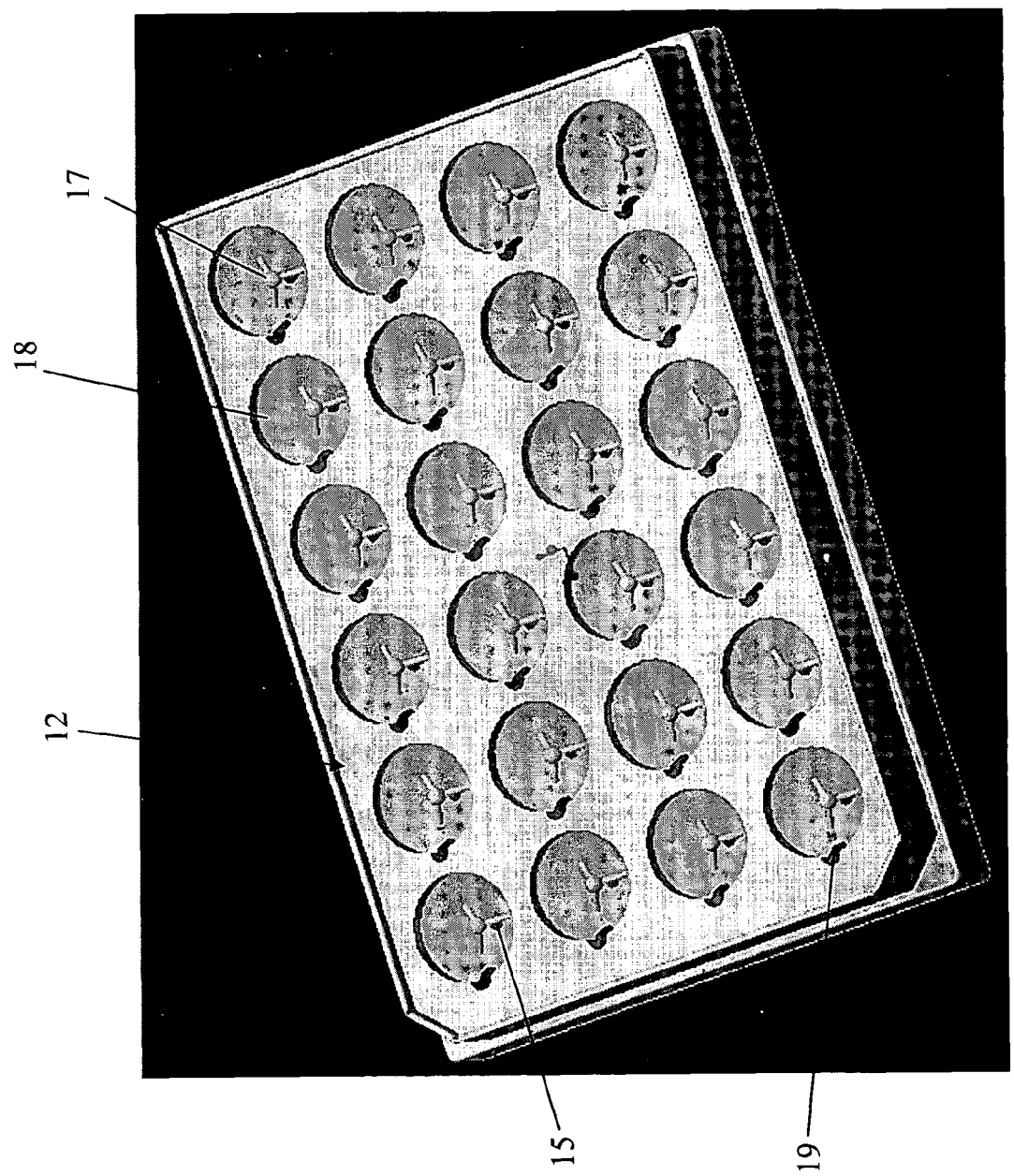
FIG. 2 is a perspective view of one embodiment of a perfusion unit of the bioreactor system shown in FIG. 1.

In a preferred embodiment, perfusion unit 12 is a multi-well plate including a plurality of main chambers or wells 18 configured to house or contain a cell culture. Similarly, the fluid source unit 14 may comprise one or more separate multi-well plates including a plurality of fluid reservoir chambers or wells 20 to store fluid, such as cell culture media. In operation, each main chamber or well 18 is in fluid communication with a corresponding individual fluid reservoir chamber 20. In a preferred embodiment, top perfusion unit 12 and fluid source unit 14 include 24 chambers or wells, however, in alternative embodiments any number of chambers or wells may be provided. For example, the wells of top perfusion unit 12 and the fluid source unit 18 may be miniaturized to comprise 48 wells per plate, 96 wells per plate, or smaller. Similarly, pumping components may be miniaturized to comprise a smaller bioreactor system with a similar footprint, or increasing the footprint to have more individual perfusion units on one system. Referring to FIG. 2, one example of a multi-well perfusion plate 12 is shown wherein each well includes a passage or hole 15 extending through the base of the well to permit the passage of fluid therethrough. A triangulated post structure 17 is fixed onto a base portion of each well 18 and extends above hole 15. Post structure 17 facilitates the attachment of a cell adherent structure or scaffold 22 (shown in FIG. 4) to grow cell cultures. Each well may also contain a fluid return pathway 19. In one preferred embodiment, perfusion unit 12 and fluid source unit 14 may be made from polystyrene, polycarbonate, polypropylene, other plastic, or any other suitable material, and may be injection molded in parts or in their entirety.

In another preferred embodiment, perfusion unit 12 and fluid source unit 14 are preferably configured and dimensioned to be removably coupled to pumping unit 16. Accordingly, perfusion unit 12 and fluid source unit 14 may be interchangeable components of the system, such that a plurality of like units or plates may be exchanged or removably coupled to pumping unit 16 as desired. For example, the fluid source unit 14 is configured to be removably coupled to the pumping unit 16 such that the fluid source unit 14 may be re-usable or disposable for media addition. Similarly, perfusion unit 12 may be removed from one pumping unit 16 to another to associate cell cultures with different fluid/dynamic environments.

Figure 3:
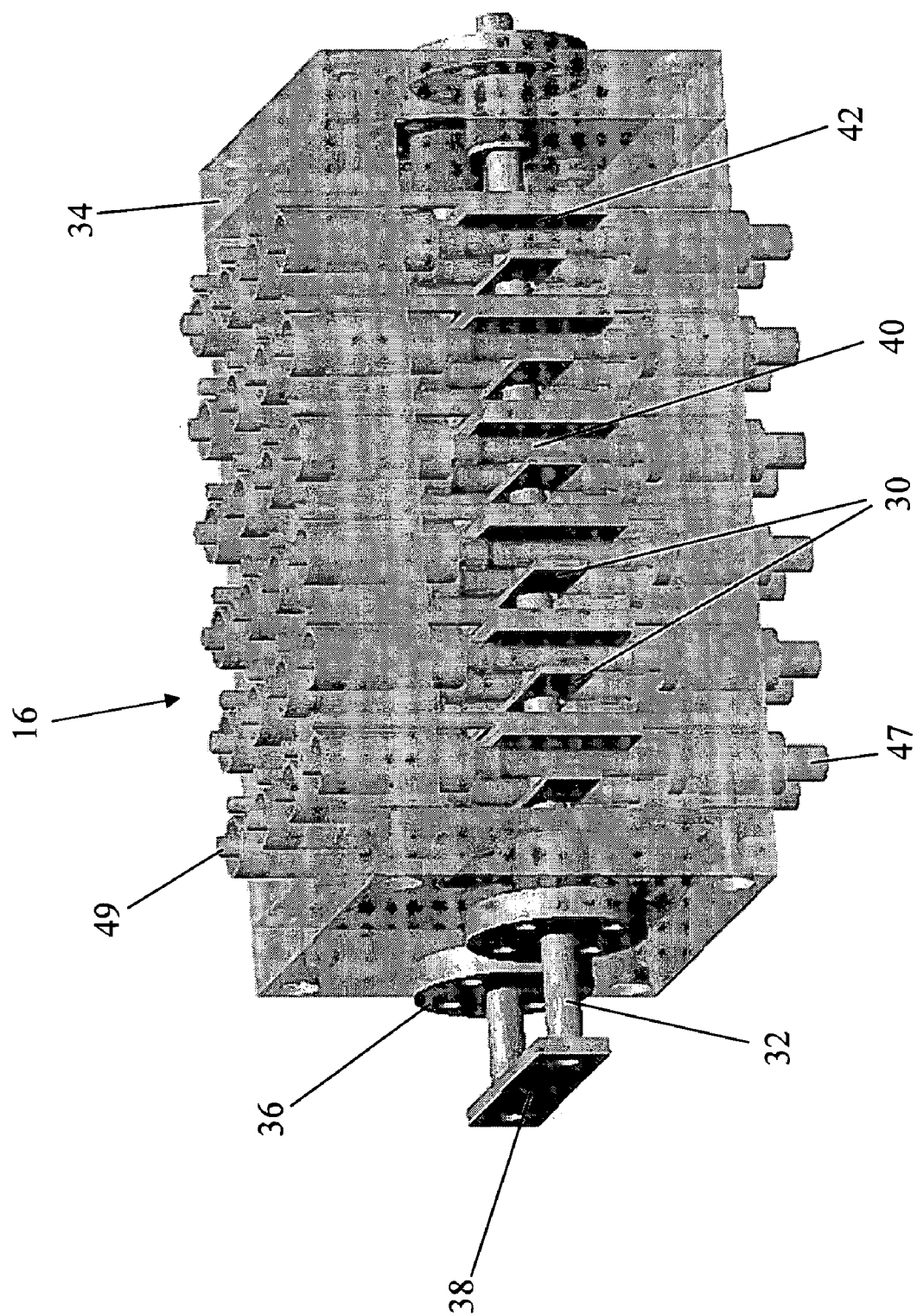
FIG. 3 is a perspective view of one embodiment of a pumping unit of the bioreactor system shown in FIG. 1.
Figure 4:
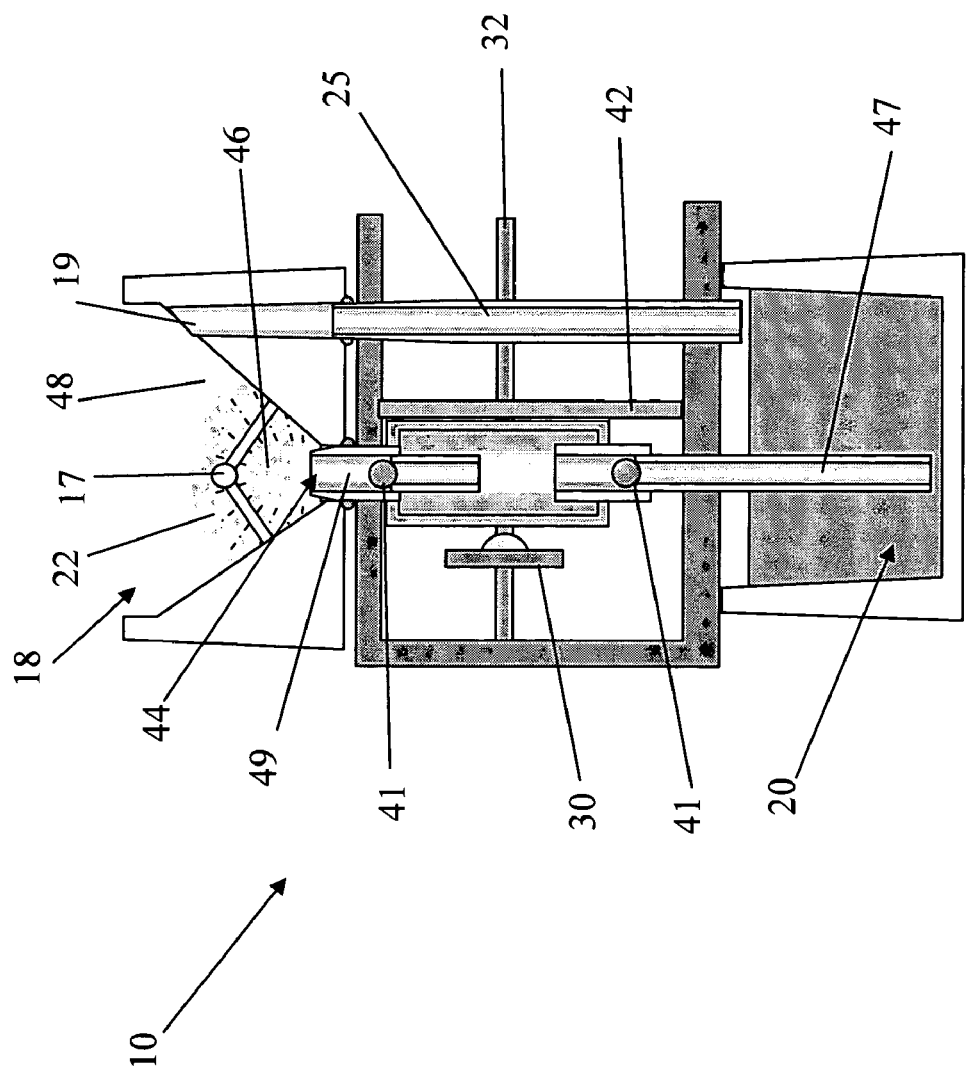
FIG. 4 is a cross-sectional exploded view of a bioreactor unit of the system of FIG. 1.

Pumping unit 16 comprises an array of fluid connectors and/or hardware components to fluidly connect each main chamber 18 with each fluid reservoir chamber 20. In a preferred embodiment, pumping unit or station 16 may comprise any hardware components suitable for transferring or pumping fluid from the fluid source unit 14 to the perfusion unit 12 such as, for example, motorized pump(s), valves, tubes, pipes, or other devices or means for pumping or transferring the fluid. Generally, any type of pumping mechanism may be used, including but not limited to peristaltic, centrifugal, vibrating, piezo, or an air or fluid driven pumping mechanism, or individual electronic pumps wherein each perfusion unit could be programmed with a different pumping rate. In a particular preferred embodiment, shown in FIG. 3, pumping unit or station 16 utilizes a peristaltic pumping mechanism including an array of pumping plates 30 mounted upon driving rods 32. Rods 32 are slidably mounted to housing 34 in bearings 36 and in operation are driven back and forth along the axis of rods 32 by a motor attached to coupling plate 38. When rods 32 are driven, pumping plates 30 squeeze flexible tubing 40 against static plates 42 to pump the fluid contained in flexible tubing 40. As best seen in FIG. 4, single direction valves 41 are provided on either side of flexible tubing 40 and interposed between an inlet tube 47 and an outlet tube 49 to pump or direct fluid flow in one direction from the fluid reservoir chambers 20 of fluid source unit 14 toward the main chambers 18 of perfusion unit 12. A return pathway 19 is preferably built into each main chamber 18 of perfusion unit 12 which fluidly connects to return pathway 25 pumping unit 16 to provide for fluid return to the fluid source unit 14 from the perfusion unit 12, thereby creating a plurality or array of individual and separate bioreactor units 10. In this regard, when perfusion unit 12 and fluid source unit 14 are coupled to pumping unit 16, each bioreactor unit 10 is an independent fluidly self-contained entity.

Referring to FIG. 4, a cross-sectional view of an exemplary individual bioreactor unit 10 is shown, wherein each bioreactor unit generally includes a single main chamber or well 18 in fluid communication with the fluid source, housed for example in a single fluid reservoir chamber or well 20. A cell adherent structure or scaffold 22 is preferably housed within each main chamber 18 to facilitate high density cell culture growth. In this embodiment the cell adherent structure is a three-dimensional scaffold, such as a porous body having a plurality of three-dimensional cell adherent surfaces, however, in alternate embodiments, the cell adherent structure may be two-dimensional, such as a slide or plate having a two-dimensional cell adherent surface. In other alternate embodiments, the cell adherent structure may have varied shapes such as, for example, a tubular or cylindrical shape, such that a transplantable medical device/implant with a biological component may be engineered in a high throughput device. In this regard, cells and/or tissue may adhere or grow upon the tubular structure to grow cell or tissue containing tubes such as, for example, vascular grafts, stents, neural tubes, shunts, etc., for transplantation into the body of a patient. In other embodiments, cartilage and/or bone may be grown or engineered in a predetermined shape.

In a preferred embodiment, the cell adherent structure is coupled to the main chamber about a fluid port 44 such that the fluid flows directly into or about the cell adherent structure. For example, a three-dimensional scaffold 22 may be coupled, molded, bonded, synthesized, or otherwise attached to the main chamber 18 such that a stem or fluid port 44 extends into the central portion or interior of the scaffold when, for example, perfusion plate 12 is coupled to pumping unit 16. In another preferred embodiment, each main chamber 18 of perfusion plate 12 is configured to receive scaffolds that may be coupled, fastened, or otherwise connected to a portion of each main chamber 18 by any suitable means known to those skilled in the art. In one preferred embodiment, scaffold 22 may be releasably plugged into or attached to main chamber 18.

The scaffolds can be made from any type of polymer, ceramic, metal or mixture of any type suitable for adhering cells thereto. In a preferred embodiment, the scaffold is made from a hydrogel-based material, which may be synthesized from covalently crosslinked alginate, hyalrunic acid or a blend of the two polysaccharides at any mixing percentage as desired. For example, the mixing percentage may be tailored to achieve a desired degradation profile for the final application. In alternate embodiments, the scaffolds may be made of other suitable materials, such as those disclosed in U.S. Patent Publication No. 2004/0147016 entitled "Programmable scaffold and methods for making and using same", the entire contents of which are incorporated by reference. In one preferred embodiment, the scaffold may be a porous structure having randomly aligned pores. In alternative embodiments, scaffolds may be used that have directionally aligned pores such that a less random pore pattern may be attained and fluid flow may be further assured of navigating or flowing through all of the pores of the scaffold. In alternate embodiments, the scaffolds may be modified with any number or type of cell signaling or cell interacting molecule, such as those disclosed in U.S. Patent Publication No. 2004/0147016, entitled "Programmable scaffold and methods for making and using same," the entire contents of which are incorporated by reference.

In operation, fluid is pumped directly into the internal scaffold structure and may perfuse or flow from the interior 46 of scaffold 22 to the exterior 48 of scaffold 22. In one preferred embodiment, fluid is pumped at a rate ranging from about 10 to 0.1 milliliters per minute. In this regard, fluid may readily flow through the internal pores of the scaffold as opposed to circumventing the scaffold or flowing mainly along the exterior of the scaffold. The enhanced diffusion mass transport provided by the perfused fluid flow advantageously allows metabolites and nutrients to diffuse into and out of scaffold 22. In this regard, perfusion culture permits long term tissue engineering experiments allowing growth of high density cell cultures to mimic tissues.

In prior art devices where fluid is permitted to circumvent the scaffold, severe oxygen limitations may be caused because oxygen is consumed by the cells adhered upon the outside of the scaffold and cells adhered upon the inside of the scaffold may be oxygen starved.

Figure 5:
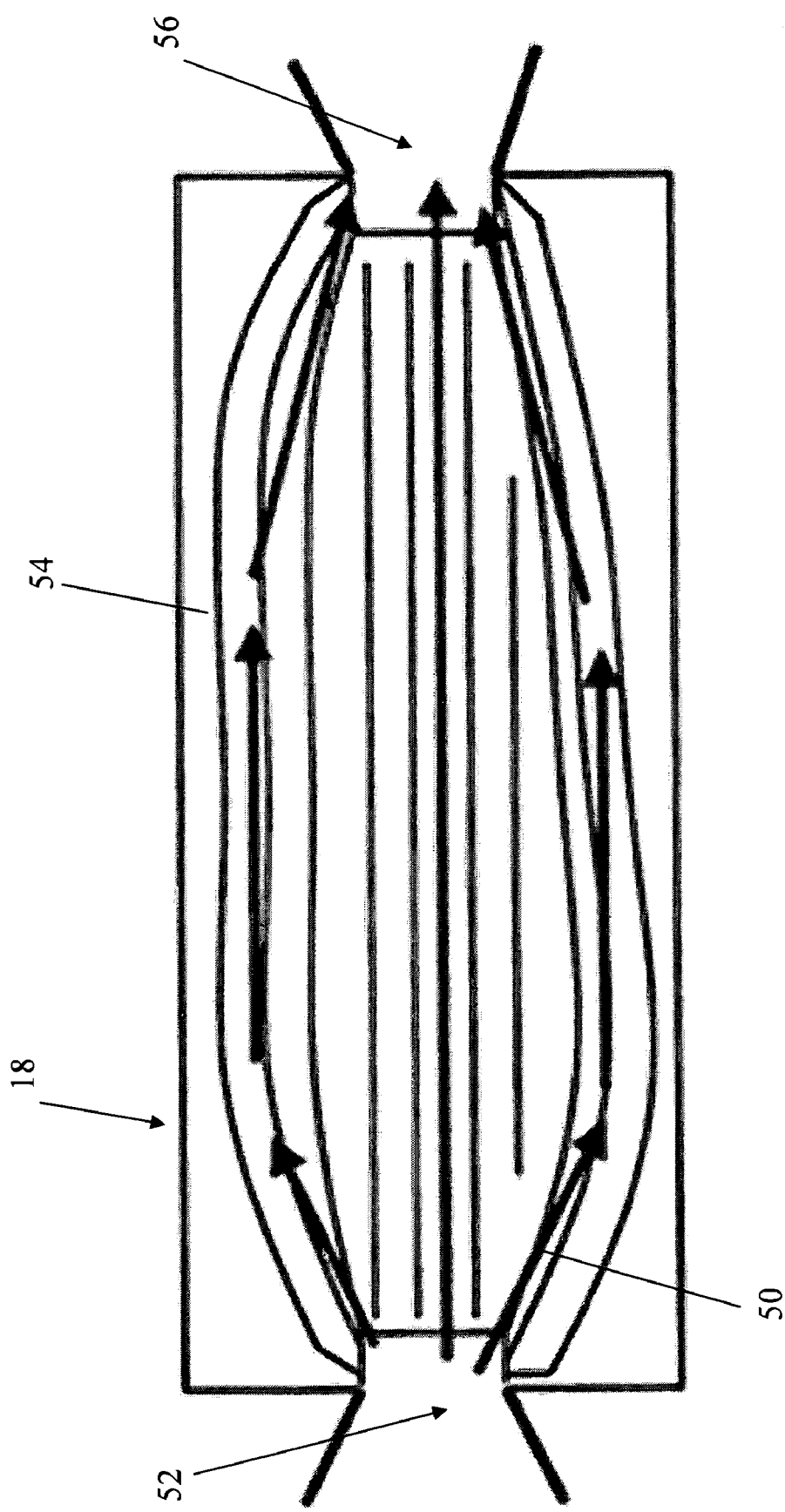
FIG. 5 is a cross-sectional view of another embodiment of a bioreactor system according to the present invention.

Referring to FIG. 5, an alternative embodiment of a main chamber 18 is shown wherein the fluid flow 50 is directed from an inlet 52 through an alternative scaffold 54 and exits the scaffold and chamber at an outlet 56 as opposed to flowing randomly throughout the scaffold.

Figure 6:
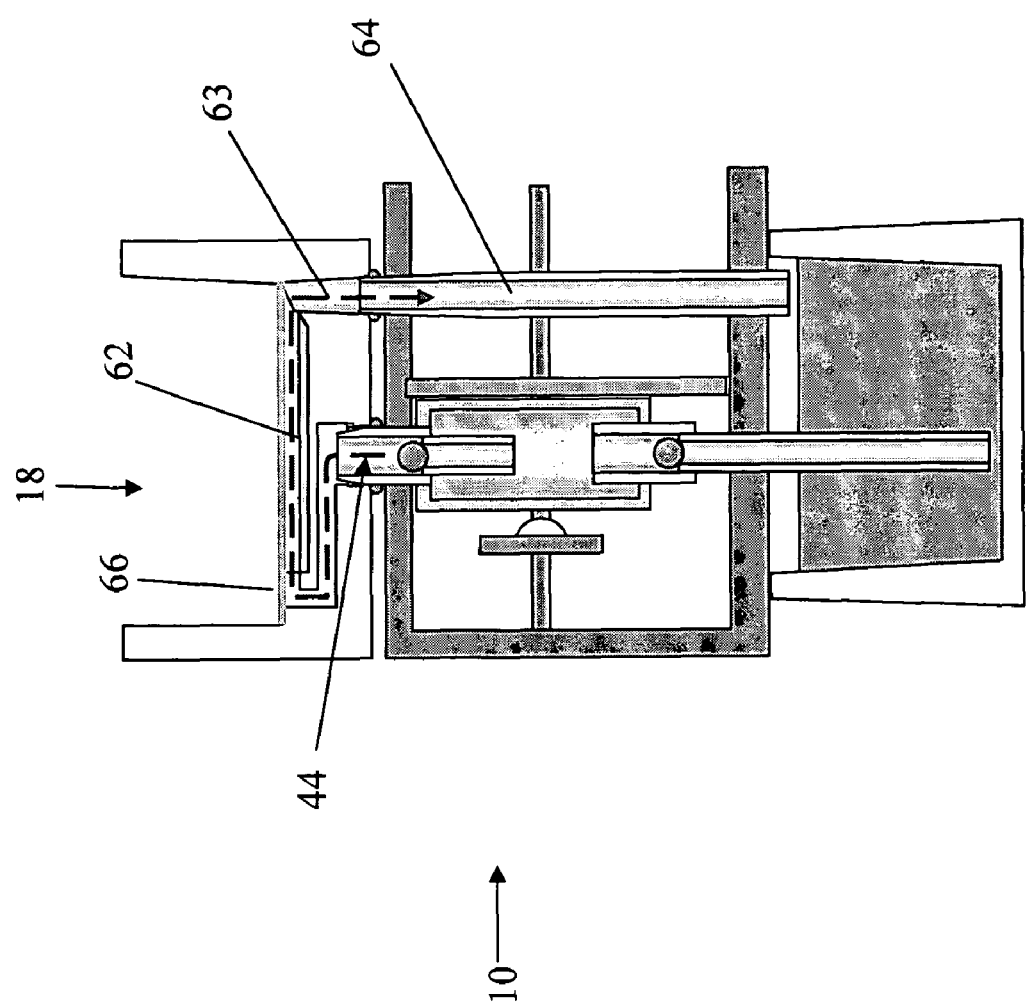
FIG. 6 is a cross-sectional view of another embodiment of a bioreactor system according to the present invention.

Referring to FIG. 6, another alternative embodiment of a bioreactor unit 10 is shown wherein main chamber 18 includes a two-dimensional cell adherent structure 62 with a cell adherent upper surface. In this embodiment, the cell adherent structure 62 is coupled to the chamber 18 such that fluid may flow along path 63 through fluid port 44 and across the two-dimensional surface of structure 62 and returns through return pathway 64. A plate 66 covers structure 62 and is spaced therefrom to contain the fluid such that the fluid flows directly over the cell adherent surface.

Figure 7:
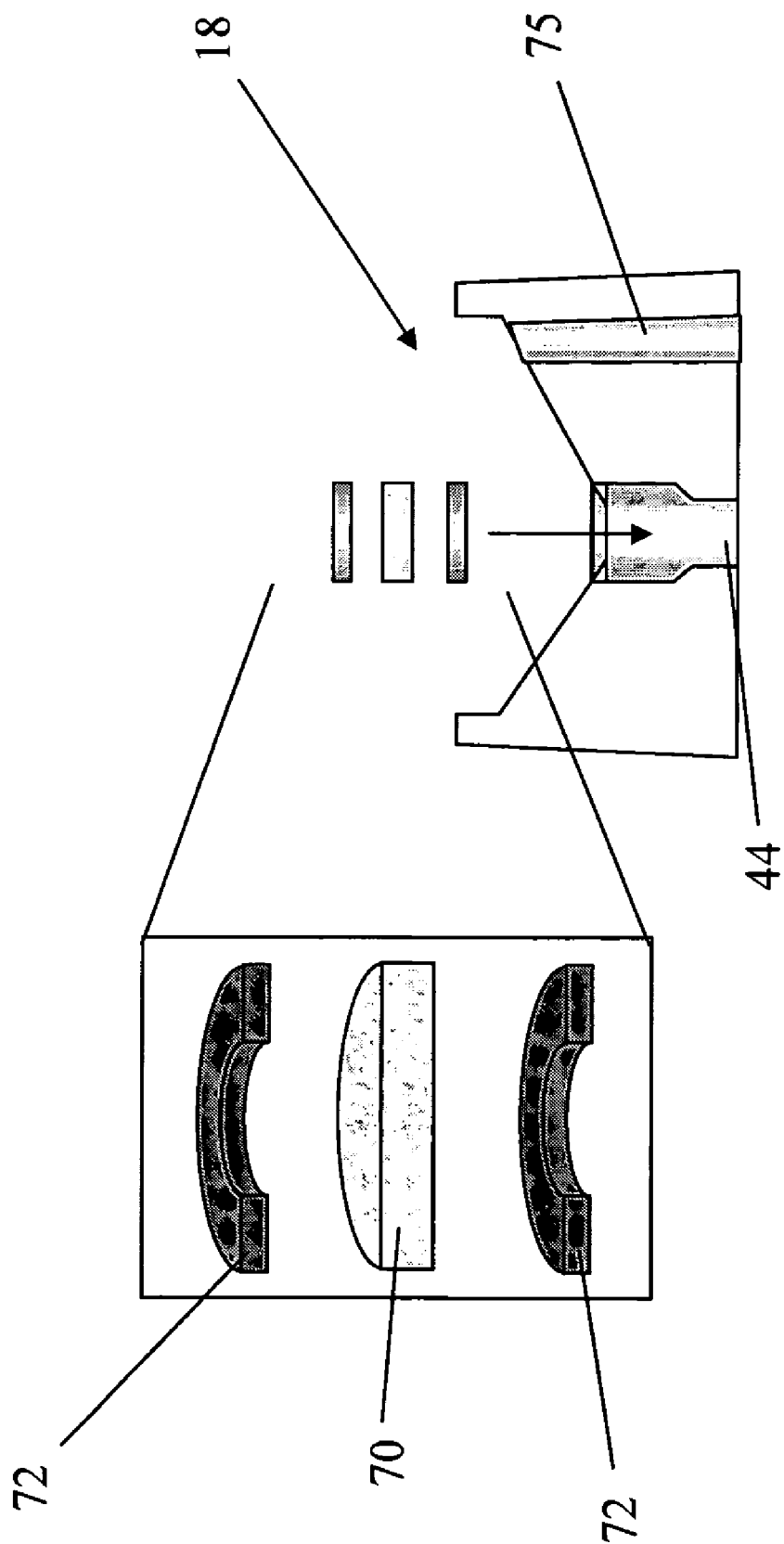
FIG. 7 is a cross-sectional view of another embodiment of a bioreactor system according to the present invention.

Referring to FIG. 7, another alternative embodiment of a main chamber 18 is shown, wherein a cell specimen 70 may be coupled, fastened, or otherwise connected to a portion of each main chamber 18 by any suitable means known to those skilled in the art. In some embodiments, cell specimen 70 may be a cell adherent structure or scaffold and in other embodiments cell specimen 70 may comprise portions or slices of tissue. For example, cell specimen 70 may comprise liver slices, pancreatic islets, liver spheroids, 3-D tissue models (such as those commercially available from Mattek, Inc. or Regenemed, Inc.), 3-D cancer models (such as those commercially available from Mina Bissell), cells on microcarriers or fiber disks (such as those commercially available from fibracell), or any other cellular bodies that may be grown in vitro.

In one embodiment, cell specimen 70 has a cylindrical or disc shape and may be held in place in main chamber 18, for example, between a pair of washers 72. Washers 72 include a central opening to permit fluid flow therethrough. In operation, fluid may flow through port 44 and perfuse through cell specimen 70 and exit through the central opening of the top washer 72 and return via return pathway 75. In this regard, the present embodiment is configured to keep slices or cell specimens emerged at all times in media, while exposing the tissue or cell specimen to fluid flow similar to in vivo conditions and enhancing gas and nutrient transfer. In a preferred embodiment, the present system facilitates the maintaining of cell viability, and the maintaining of the specimens or tissue slices in a format for drug testing. The configuration of this embodiment may be advantageously utilized with, for example, tissue slices or scaffolds made of polymer or ceramic material or other materials that cannot be synthesized in place.

Figure 8:
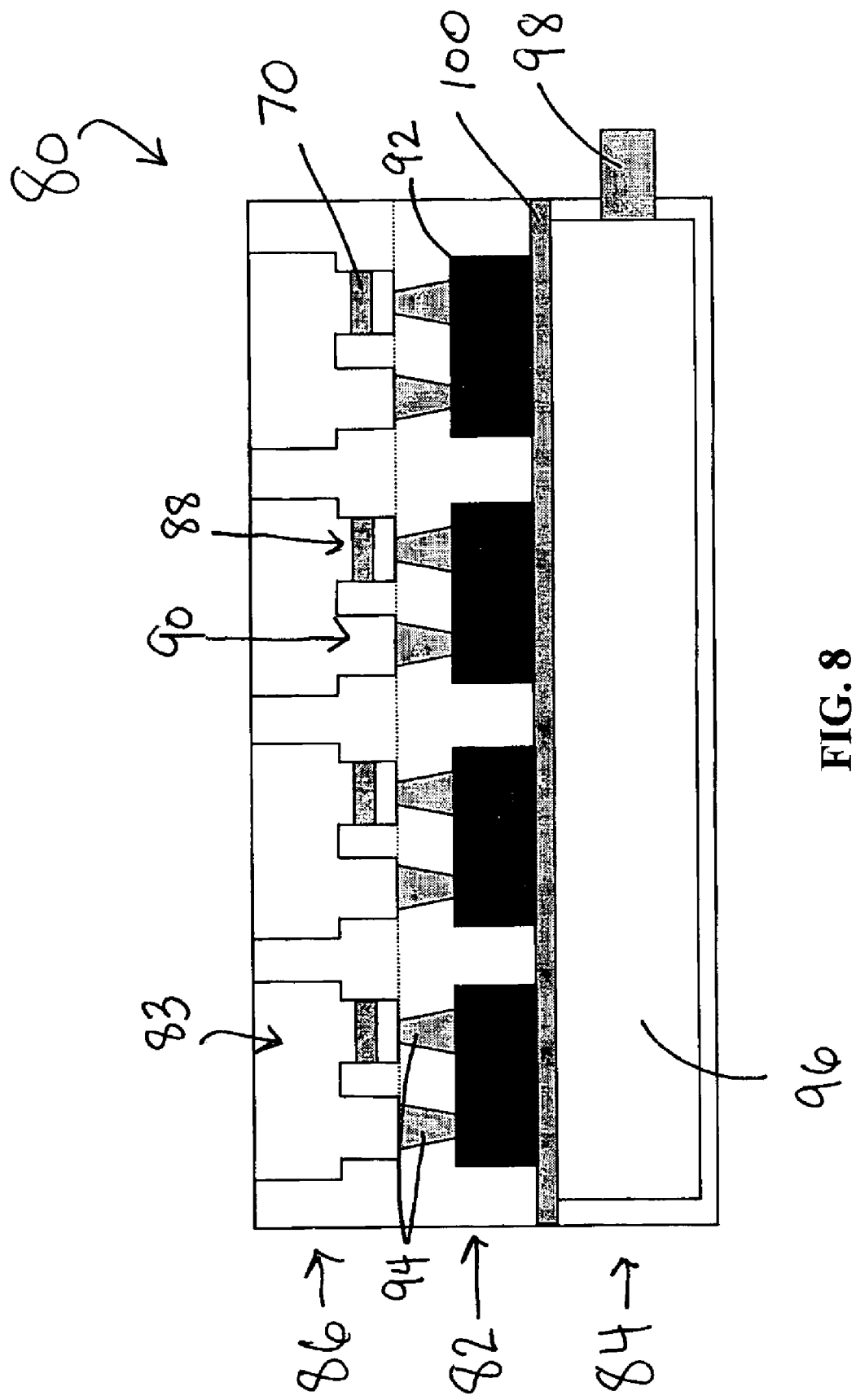
FIGS. 8-10 are cross-sectional views of another embodiment of a bioreactor system according to the present invention.
Figure 9:
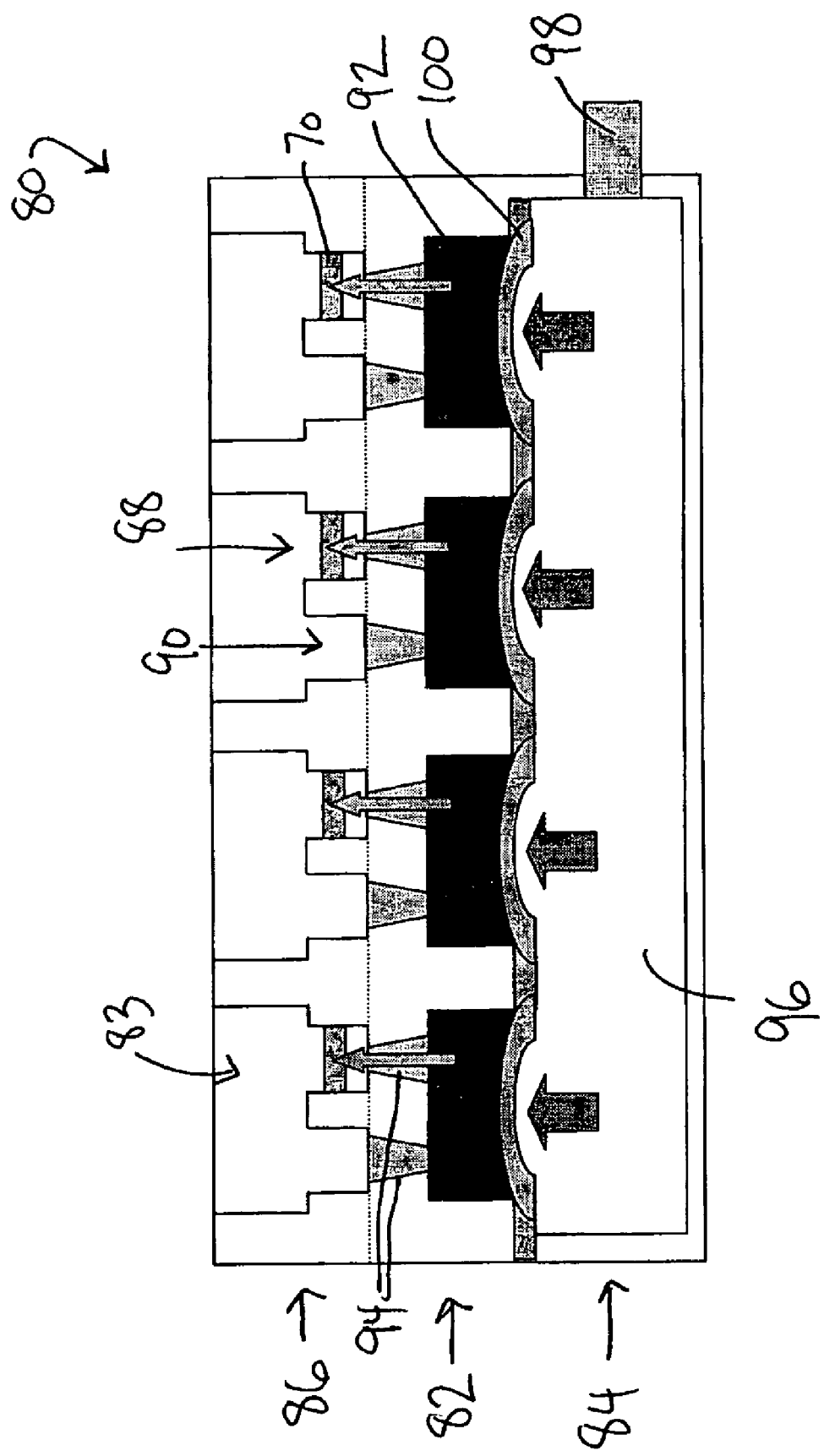
Figure 10:
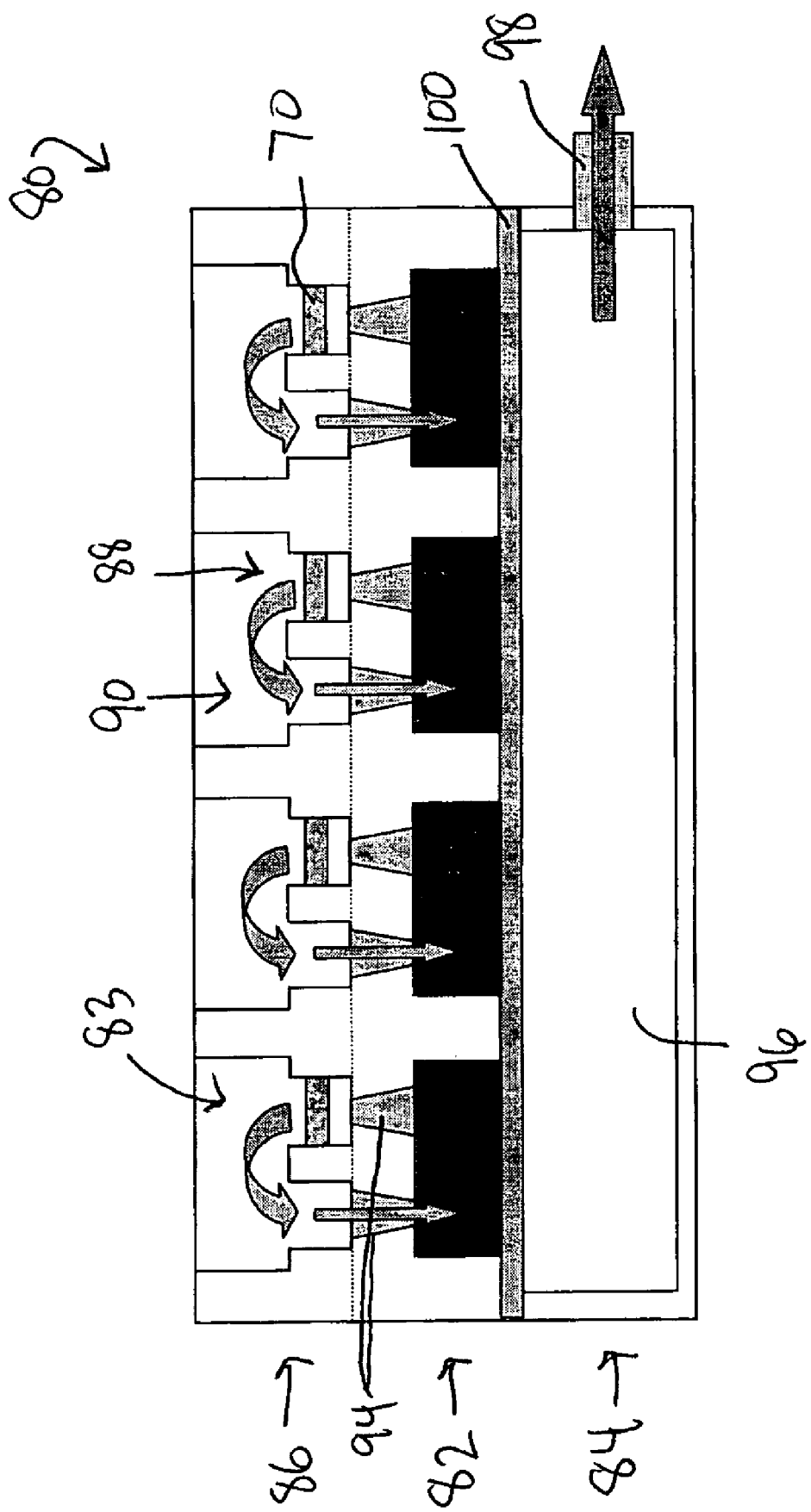

Referring to FIGS. 8-10, an additional embodiment of a bioreactor system 80 is shown. In general, bioreactor system 80 is a pneumatic system comprising three disposable or reusable pieces or components: a bottom reservoir plate 82 configured to contain media, a pumping device 84 that induces the motion of the media, and a top perfusion plate 86 that mates with the bottom reservoir plate and pumping device, and is configured to maintain the position of the tissue slices or cell specimen 70 in the media flow and create a closed fluid path for the media to return to bottom reservoir plate 82. Both the bottom reservoir plate and the top perfusion plate generally include multiple wells or chambers 83 and each plate may be injection molded and may be disposable or reusable items. Also, the plates may be sterilized using any suitable sterilization method known to those skilled in the art. Each well of the perfusion plate 86 generally comprises an inlet portion 88 and an outlet portion 90. Each well of the bottom reservoir plate 82 generally comprises a fluid reservoir 92 and a pair of one-way valves or check valves 94. In one embodiment, the one-way valves may be molded into a one piece plate. Each of the pair of one-way valves is aligned with the corresponding inlet and outlet portions 88, 90 of the perfusion plate to direct and or allow the fluid or media to flow from fluid reservoir 92 into the inlet 88 and out of the outlet 90 and return to the fluid reservoir 92. In one embodiment, cell specimen 70 may be positioned within the inlet portion 88 of each well of the perfusion plate 86. In one variation, two mesh discs and a retaining ring may be used to retain the tissue slice or cell specimen 70 in position on the perfusion plate. The optimal geometry and orientation of the cell specimen may vary depending on the tissue type. For example, the tissue may be oriented vertically or horizontally to the fluid flow.

The pumping device 84 of the present embodiment generally comprises a pressure chamber 96 having an air inlet 98 and a flexible diaphragm 100 that interfaces with the bottom reservoir plate 82. As best seen in FIG. 9, in operation, air pressure is introduced through inlet 98 into the pressure chamber 96 and the flexible diaphragm 100 expands and exerts pressure on the fluid reservoirs 92 of the bottom plate 82 causing the upward flow of media or fluid. As shown in FIG. 10, when the air pressure is released through inlet 98, the diaphragm 100 contracts, releasing pressure on the fluid reservoirs 92 and drawing or inducing the downward or return flow of media or fluid. One advantageous feature of the present embodiment is that the media or fluid is self-purging or actively drained as opposed to gravity-driven. In this regard, once the well of the perfusion plate contains media or fluid, the pumping device 84 purges the perfusion plate well during operation. In one embodiment, the pumping device may be disposable or reusable. Also, the pumping device may be sterilized using any suitable sterilization method known to those skilled in the art. Several variations of the multi-well plate pumping device may also be used, including electric, peristaltic, and other diaphragm pumping techniques known to those skilled in the art.

Figure 11:
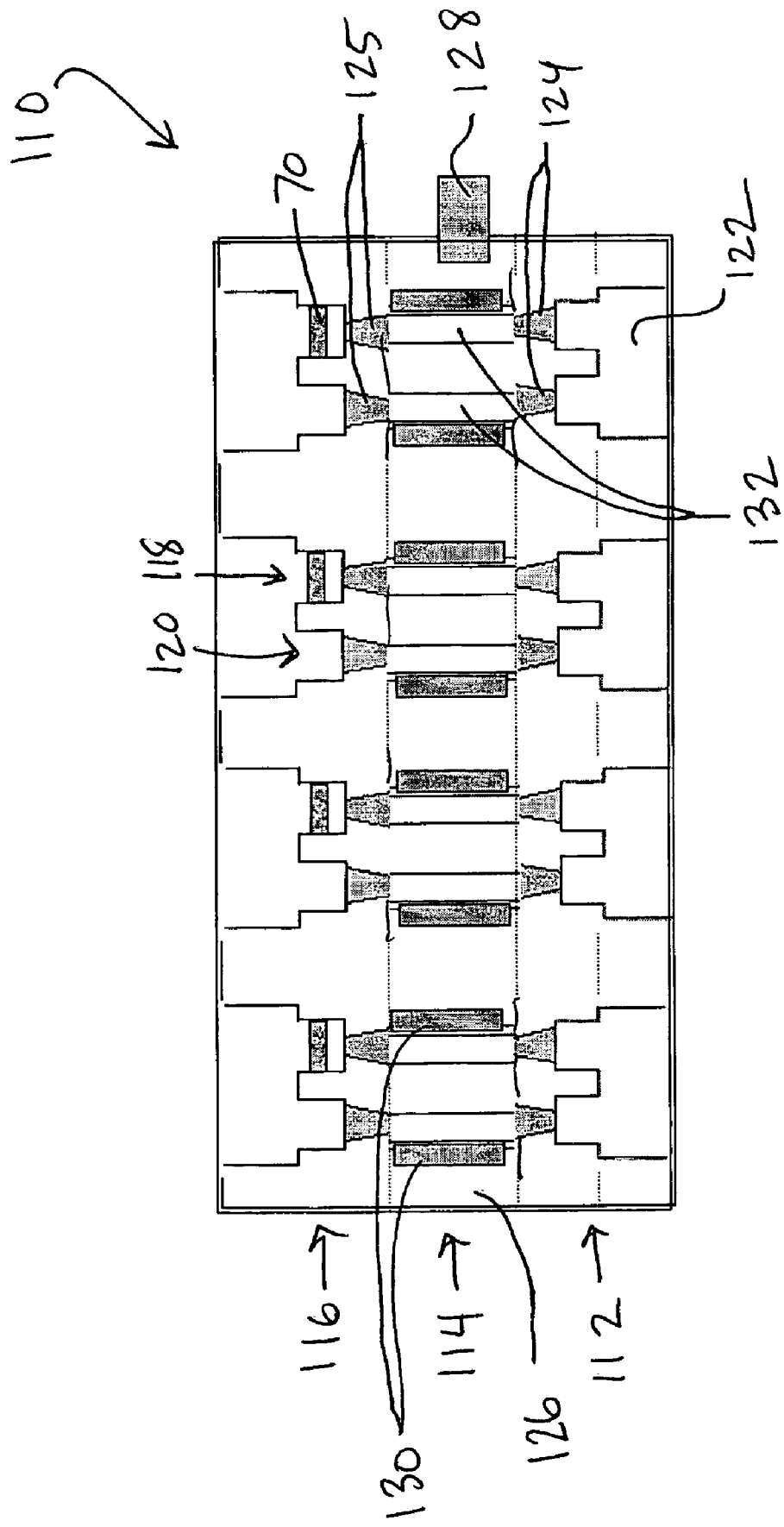
FIGS. 11-12 are cross-sectional views of another embodiment of a bioreactor system according to the present invention.
Figure 12:
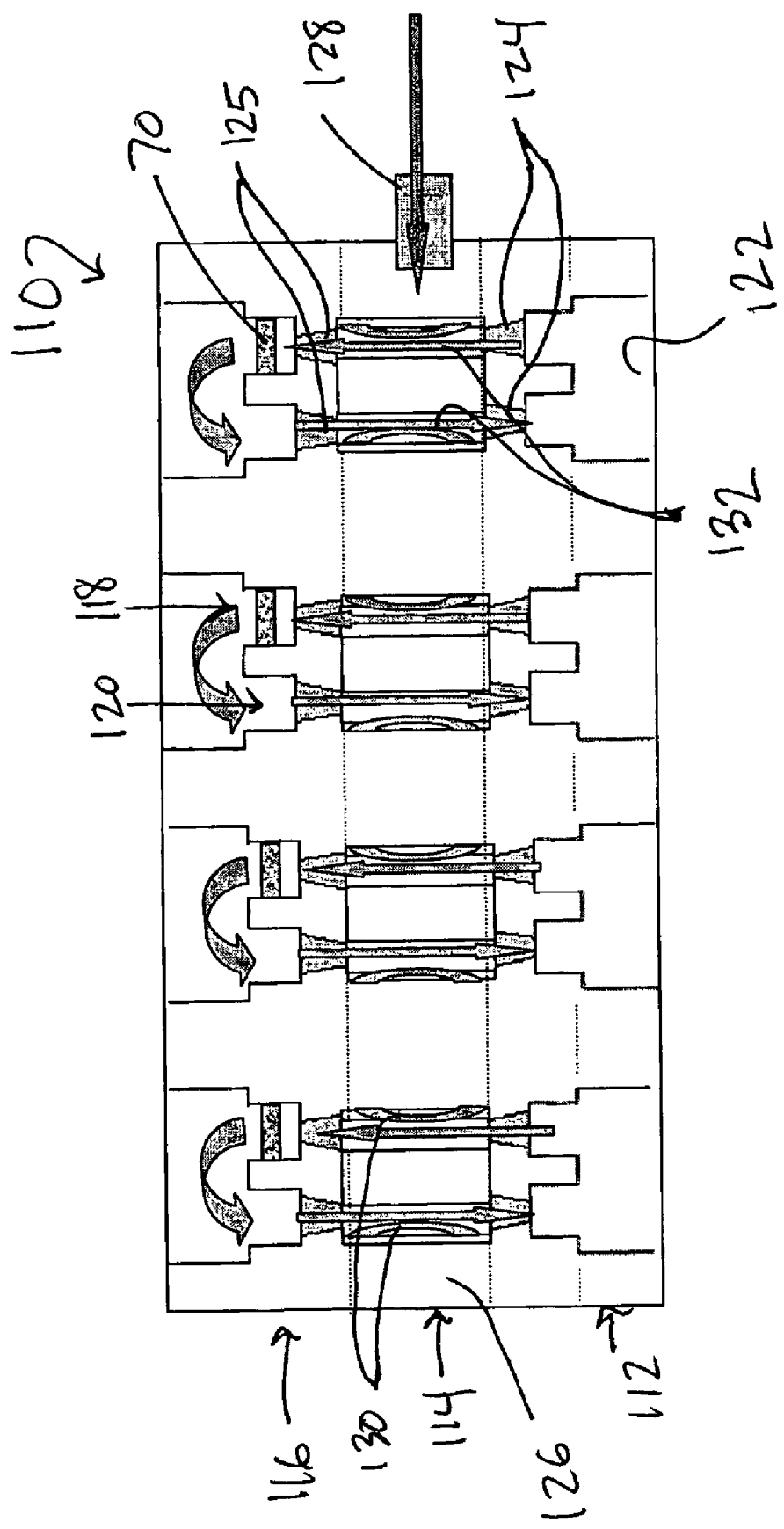
Figure 13:
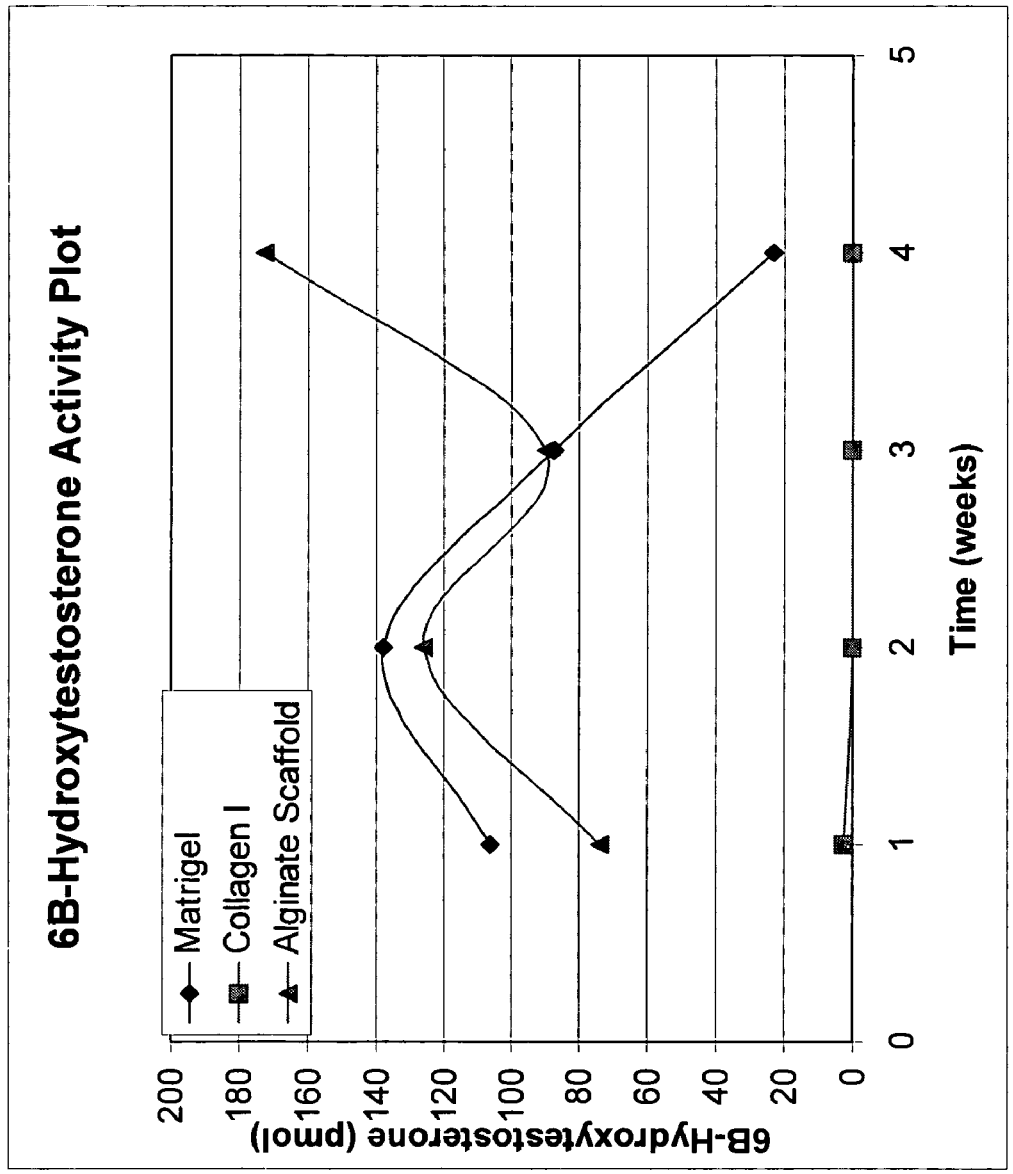
FIG. 13 is a graphical representation of one example of a cell biology experiment performed according to the invention showing hepatocytes growth on scaffolds with perfusion.

Referring to FIGS. 11-12, an additional embodiment of a bioreactor system 110 is shown. In general, bioreactor system 110, similar to bioreactor system 80, is a pneumatic system comprising three disposable or reusable pieces or components: a bottom reservoir plate 112 configured to contain media, a pumping device 114 that induces the motion of the media, and a top perfusion plate 116 that mates with the pumping device, and is configured to maintain the position of the tissue slices or cell specimen 70 in the media flow and create a closed fluid path for the media to return to bottom reservoir plate 112. Both the bottom reservoir plate 112 and the top perfusion plate 116 are substantially similar to plates 82, 86 described above and generally include multiple wells or chambers 113. Each plate may be injection molded and may be disposable or reusable items. Also, the plates may be sterilized using any suitable sterilization method known to those skilled in the art. Each well of the perfusion plate 116 generally comprises an inlet portion 118 and an outlet portion 120. Each well of the bottom reservoir plate 112 generally comprises a fluid reservoir 122 and a pair of one-way valves or check valves 124. In one embodiment, the one-way valves may be molded into a one piece plate. Each of the pair of one-way valves 124 is connected via flexible passages or tubing 132 and another pair of one-way valves 125 with the corresponding inlet and outlet portions 118, 120 of the perfusion plate to direct and or allow the fluid or media to flow from fluid reservoir 122 into the inlet 118 and out of the outlet 120 and return to the fluid reservoir 122. In one embodiment, cell specimen 70 may be positioned within the inlet portion 118 of each well of the perfusion plate 116. In one variation, two mesh discs and a retaining ring may be used to retain the tissue slice or cell specimen 70 in position on the perfusion plate. The optimal geometry and orientation of the cell specimen may vary depending on the tissue type. For example, the tissue may be oriented vertically or horizontally to the fluid flow.

The pumping device 114 of the present embodiment generally comprises a pressure chamber 126 having an air inlet 128 and a plurality of flexible diaphragms 130 that surround flexible passages 132. Flexible passages 132 extend between the fluid reservoirs 122 of the bottom plate and a pair of one-way valves or check valves 125 aligned with the inlet and outlet portions 118, 120 of the perfusion plate 116. As best seen in FIG. 12, in operation, air pressure is introduced through inlet 128 into the pressure chamber 126 and the flexible diaphragms 130 expand and exert pressure on the flexible passages or tubing 132 causing the upward flow of media or fluid through the inlet portion 118 of the perfusion plate 116 and the simultaneous downward flow of media or fluid out from the perfusion plate 116 through the outlet portion 120 to the fluid reservoir 122. One advantageous feature of the present embodiment is that the media or fluid is self-purging or actively drained as opposed to gravity-driven. In this regard, once the well of the perfusion plate contains media or fluid, the pumping device 114 purges the perfusion plate well during operation. In one embodiment, the pumping device may be disposable or reusable. Also, the pumping device may be sterilized using any suitable sterilization method known to those skilled in the art. Several variations of the multi-well plate pumping device may also be used, including electric, peristaltic, and other diaphragm pumping techniques known to those skilled in the art.

With respect to all of the aforementioned multi-well bioreactor systems, different cell types may be cultured in the same set of wells. For example, in the embodiment of FIG. 4, a hepatocyte cell may be cultured in fluid reservoir chamber 20, while an islet cell may be cultured in main chamber 18. The cells are in fluid communication via the media contained within the bioreactor unit 10 of FIG. 4. In another variation, multiple parallel wells may be in fluid communication with each other. For example, referring to the embodiment of FIG. 1, a hepatocyte cell may be cultured in well A1 of FIG. 1, while an islet cell may be cultured in well D6 of FIG. 1. All of the wells may be fluidly connected together by channels or other fluid pathways, such that after a period of time, the media from wells A1, D6, and as many of the wells in fluid communication, will mix with each other and may come to a steady state.

Utilizing the aforementioned multi-well bioreactor systems of the present invention, unique experiments may be studied that incorporate fluid flow. For example, multiple parallel experiments may be performed having substantially similar fluid flow characteristics. In this regard, highly complex environments may be created to perform experiments in a medium throughput or high throughput format. One skilled in the art could also create cultures consisting of several types of cell and tissue systems in fluid communication for studying complex metabolic diseases such as diabetes, obesity, and cardiovascular diseases to name a few. In one particular application for optimizing cell signaling environments, a variety of soluble and non-soluble signaling molecules consisting of growth factors, cytokines, extracellular matrix molecules, etc., may be tested at different concentrations, different mixing ratios, and at various times to facilitate the discovery of an optimal combination of factors to obtain a fully differentiated cell culture in vitro. These, environments may be created utilizing a variety of parenchymal cells and non-parenchymal cells from tissues including bone marrow, vasculature, skin, pancreas, liver, bone, cartilage, smooth muscle, cardiac muscle, skeletal muscle, kidney, etc. In another embodiment, cells such as endothelial cells may be used to create vascularization with the host. In alternate embodiments, one skilled in the art could also create cultures consisting of several types of tissue systems for studying complex metabolic diseases such as the metabolic syndrome. In alternative applications, several cell types may be incorporated to study fluid sheer and perfusion, for example, to determine fluid flow that most likely promotes cell-type segregation for vasculorgenesis and tissue development. In another application, the cells or tissue grown in the multi-well design may be used as a platform for testing drugs in a medium to high throughput format for direct drug testing on cells in dynamic cell cultures, either for drug discovery, drug testing, or ADMETox applications. Furthermore, sensing technology may be incorporated into the bioreactor system. For example, biosensing technology for sensing important cell culture variables such as glucose, ammonia, urea, pH, or general fluorescent detectors for monitoring metabolism of fluorescent compounds may be utilized with the system.

In one exemplary variation or application, a perfusion unit 12 may be used to grow cell cultures with preset conditions or particularly desirable characteristics which can then be later used for further experimentation and or discovery. The modularity and interchangeability of perfusion unit 12 advantageously permits the shipment and or transfer of a plurality of cell cultures which can be easily remounted on another pumping station 16 or similar device to perform further experimentation and/or drug testing or discovery.

Figure 17:
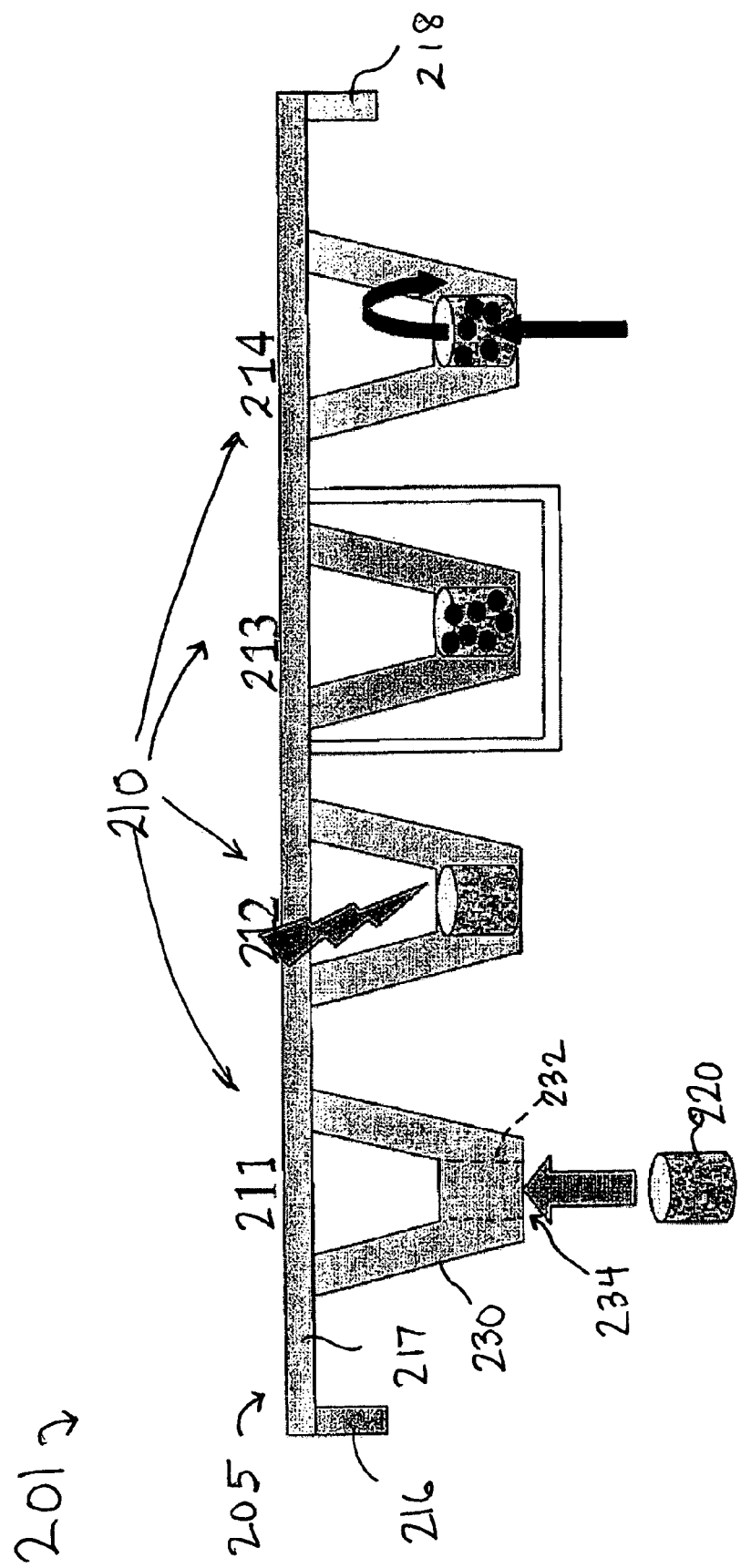
FIG. 17 is a side view of one embodiment of a system according to the present invention.
Figure 18:
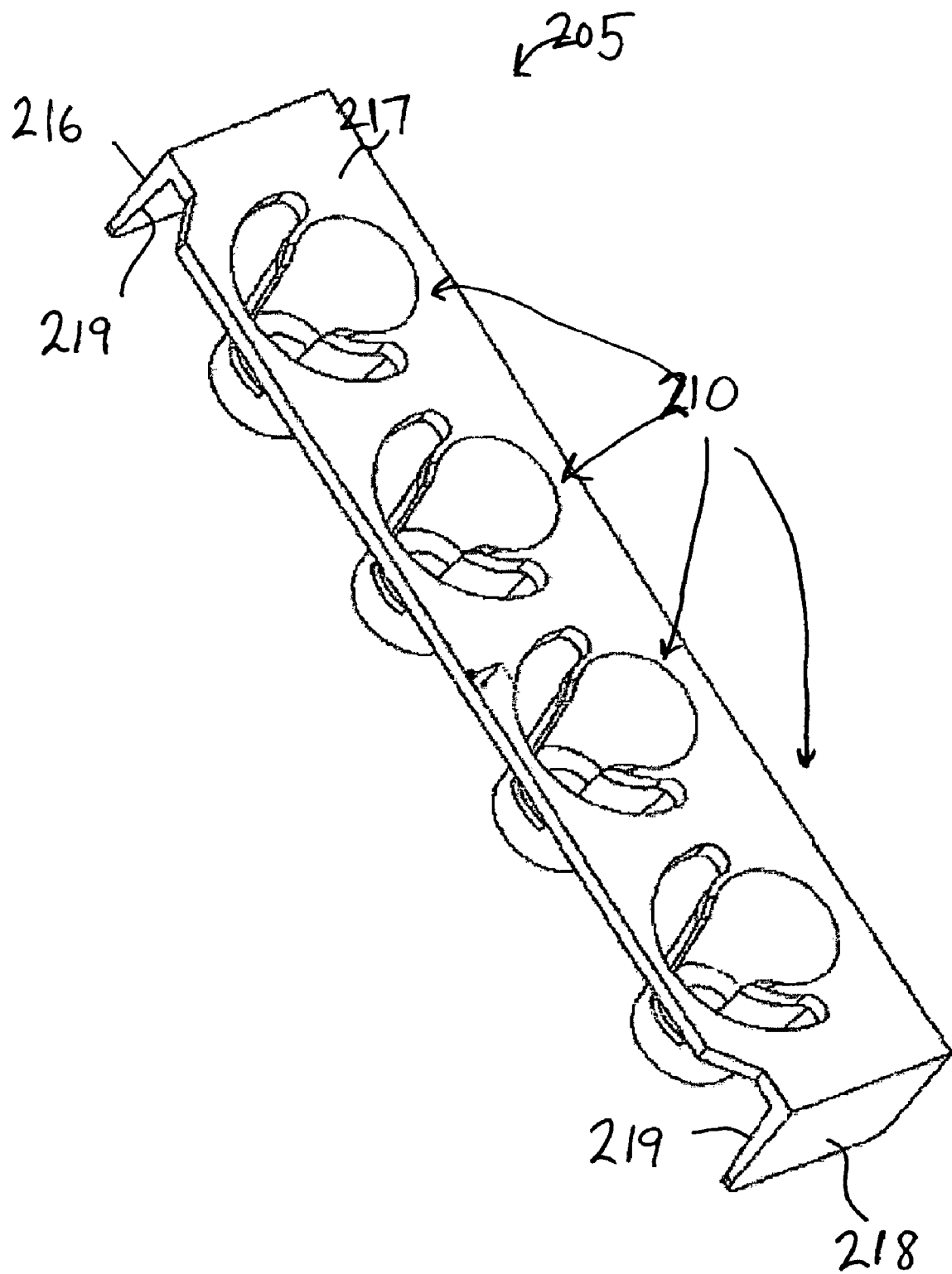
FIG. 18 is a perspective view of one embodiment of a carrier of the system of FIG. 17.

Referring now to FIGS. 17-22, a system and method for manipulating or handling scaffolds in a platform for performing biological experiments in a high throughput and/or parallel screening environment is shown. As shown in FIGS. 17 and 18, a preferred embodiment of a scaffold handling system 201 generally includes a multi-well cartridge or carrier 205 comprising an array of well units 210 wherein, in each well unit, an independent scaffold 220 may be held and a biological experiment may be performed. As shown in FIG. 17, in one embodiment, carrier 205 of scaffold handling system 201 comprises four well units 211, 212, 213, and 214 and includes sidewalls or flanges 216 and 218 extending distally from the lateral ends of cross-member 217 to mate with a multi-well plate. In alternate embodiments, however, any number or multiple of well units 210 may be included in carrier 205. For example, in one variation carrier 205 may have one well unit. In another exemplary embodiment, carrier 205 may have 8 well units. In yet another embodiment, carrier 205 may have 3 well units.

Each well unit 210 generally comprises a frustoconical or tapered body 230 exetending distally from the top of carrier 205 and includes a scaffold holding chamber 232 at the distal end 234. A cell adherent structure or scaffold 220 is preferably housed or held within each well unit 210 to facilitate high density cell culture growth. In a preferred embodiment, the cell adherent structure is coupled or loaded into to the well unit 210 about a distal end 234. For example, a three-dimensional scaffold 220 may be coupled, molded, bonded, synthesized, or otherwise attached to the distal chamber 232. In one preferred embodiment, scaffold 220 may be releasably plugged into or attached to chamber 232 for example by friction fit.

Figure 19:
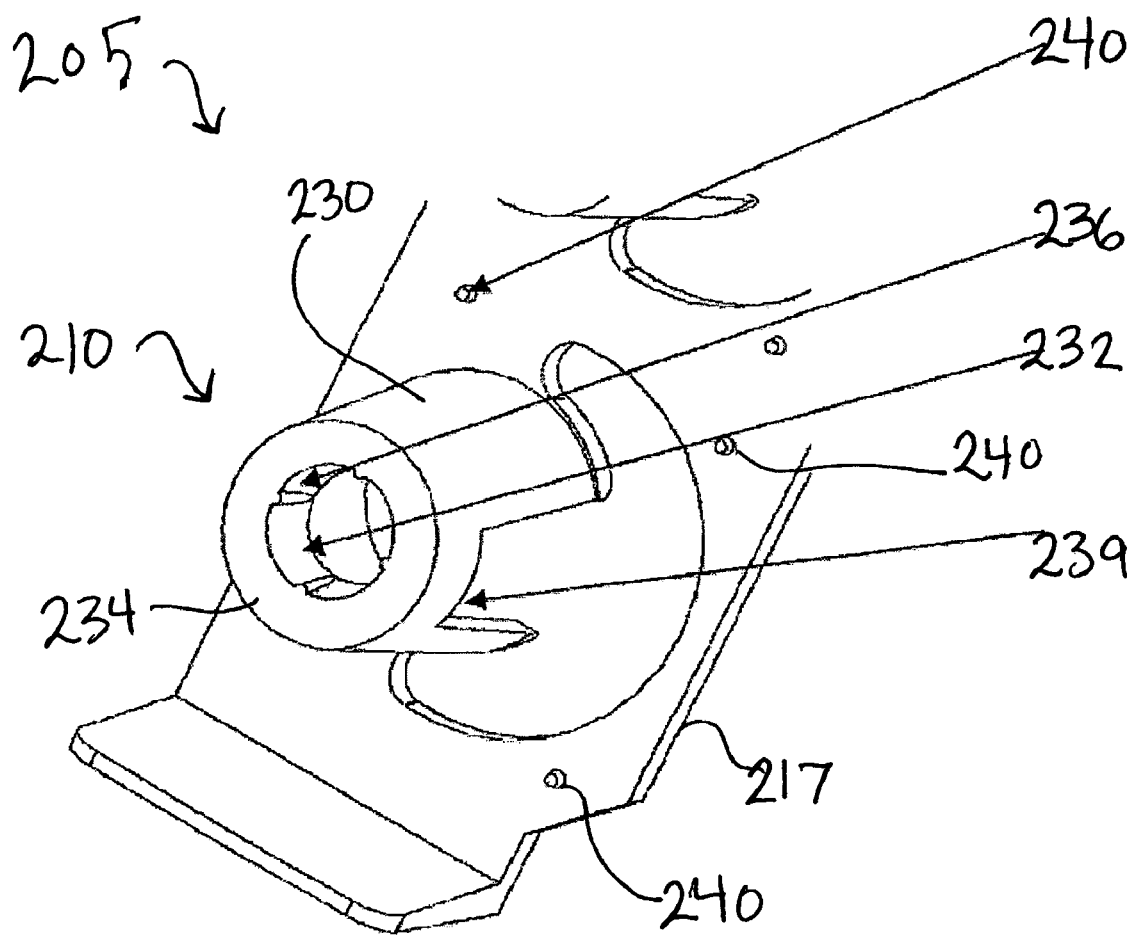
FIG. 19 is a partial perspective view of the carrier of FIG. 18 depicting a single well as seen from the bottom.

Referring to FIG. 19, a bottom perspective view of carrier 205 is shown depicting one of the well units 210. In one embodiment, scaffold holding chamber 232 is tapered, i.e. wider at the distal end of the well unit and narrower at the top or proximal end of the chamber. This tapered feature of chamber 232 may accommodate a range of scaffold sizes. For example, in one embodiment, chamber 232 may accommodate scaffolds with diameters ranging from about 4.8 mm to about 5.1 mm. In addition, one or more nubs or protrusions 236 may extend radially inward from the perimeter of chamber 232 to further grip or hold a scaffold therein by friction.

Figure 20:
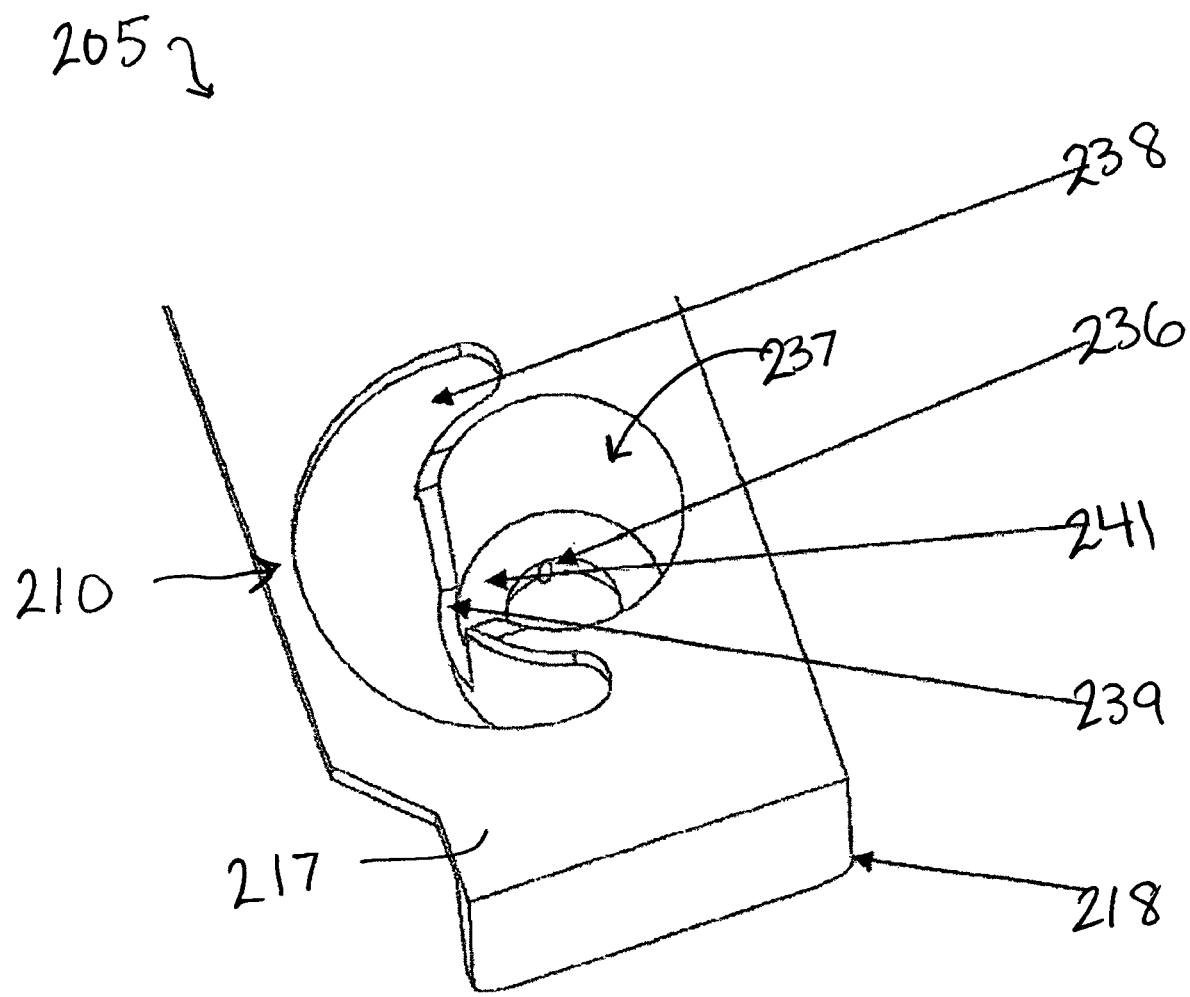
FIG. 20 is a partial perspective view of the carrier of FIG. 18 depicting a single well as seen from the top.
Figure 22:
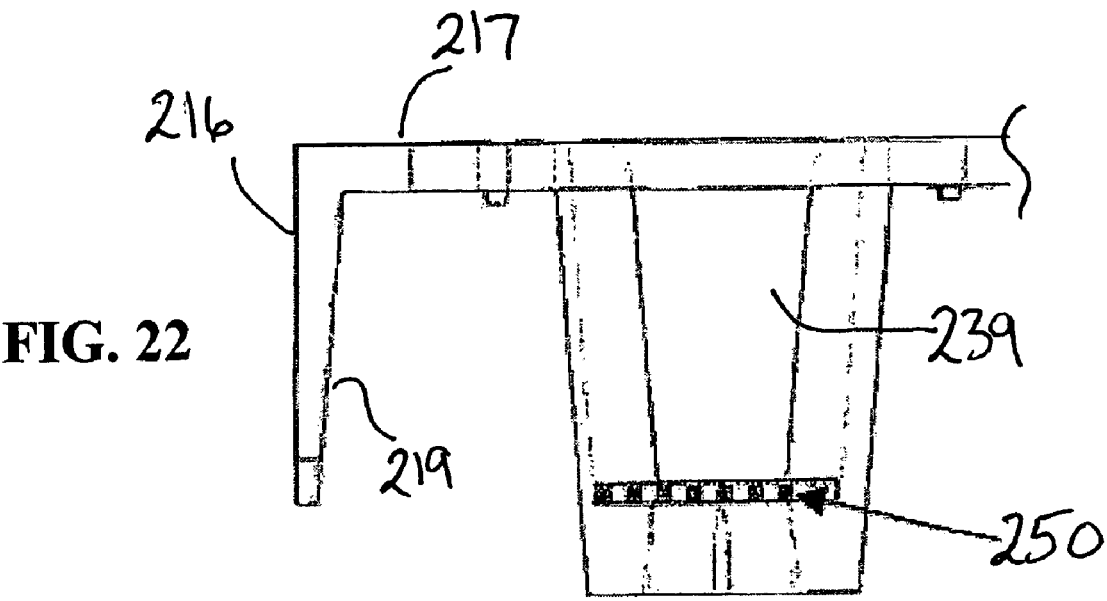
FIGS. 21 and 22 are partial side views of a single well of the carrier of FIG. 18 shown without and with a screen.
Figure 21:
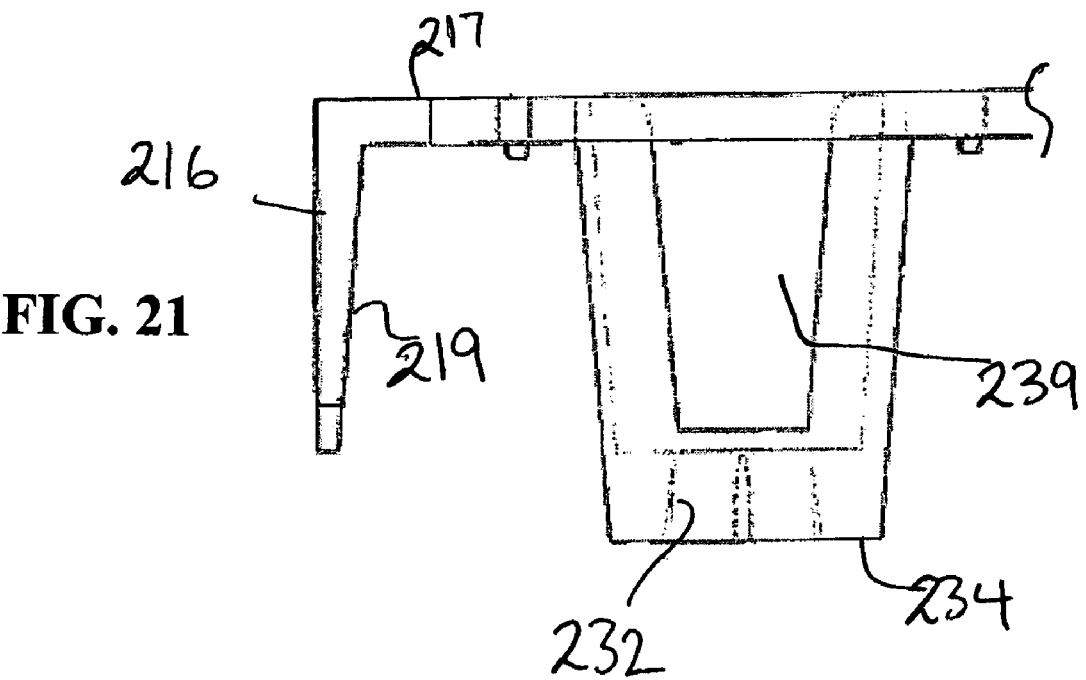

Referring to FIG. 20, a top perspective view of carrier 205 is shown depicting one of the well units 210. The top or proximal end of each well unit 210 defines an opening 237 to permit physical and visual access to a scaffold 220 held therein. In addition, a window 238 extends through the carrier 205 adjacent the well units 210 to provide access to the bottom of the well therethrough. In this regard, the open top of each well unit 210, i.e. opening 237 and window 238, facilitate aspiration or pipetting within the well unit. As best seen in FIGS. 20 and 21, in one embodiment, a longitudinal slot, channel, or opening 239 extends along a lateral portion of body 230. Opening 239 facilitates fluid overflow and permits perfusion circulation when carrier 205 is used in combination with a perfusion bioreactor as described in more detail below. As also can be seen in FIG. 21, a ledge 241 may be provided adjacent the distal end of body 230 to accommodate a screen to hold scaffold 220 in a longitudinal direction, entrap cells or minimize particulate flow. For example, as shown in FIG. 22, screen 250 may be positioned and/or molded adjacent ledge 241 to prevent movement of scaffold 220 in the proximal direction while permitting fluid flow therethrough.

Scaffold handling system 201 and carrier 205 of FIGS. 17 and 18 are configured and dimensioned to be used with a multi-well plate having a plurality of main chambers or wells to house or contain a cell culture or cell culture experiment. Multi-well plates are well known to those skilled in the art. Exemplary multi-well plates include the BD Falcon™ multi-well plates, available in 24-well plates and 96-well plates. In this regard, carrier 205 of the present embodiment is configured and dimensioned to be inserted into and/or mate with such a 24-well plate. In operation, carrier 205 may be placed across a single row of the 24-well plate with each of the well units 211, 212, 213, and 214, extending into a corresponding well of the 24-well plate so that biological experimentation may be conducted. Multiple carriers 205 may be placed aver additional rows of the multi-well plate such that a scaffold may be held in each well of the multi-well plate. In other words, for a 24-well plate, six carriers 205 may be utilized with the 24-well plate. Of course, one skilled in the art will appreciate that any number of arrays and configurations may be utilized such that the entire multi-well plate may include a cell adherent scaffold.

Sidewalls or flanges 216, 218 of carrier 205 extend distally from the lateral sides of carrier 205 and are configured and dimensioned to extend about the lateral outside of the multi-well plate to accurately mate carrier 205 with the 24-well plate. As best seen in FIG. 18, flanges 216 and 218 may have a chamfered edge 219 for easy repositioning with respect to the multi-well plate. In addition, as best seen in FIG. 19, one or more nubs, locating pins, or protrusions 240 may be provided on the underside of carrier 205 to facilitate the alignment of carrier 5 with the individual wells of a multi-well plate. In this regard, the combination of protrusions 40, flanges 16, 18, and the geometry of carrier 205 lead to a reliable and repeatable system to hold scaffolds in place with respect to a multi-well plate.

In yet another embodiment, scaffold handling system 201 and carrier 205 of FIGS. 17 and 18 may also be used with a multi-well plate of the aforementioned perfusion bioreactor. In this regard, carrier 205 of the present embodiment is configured and dimensioned to be inserted into and/or mate with such a multi-well plate of a perfusion bioreactor. In operation, carrier 205 may be placed across a single row of the multi-well plate of the perfusion bioreactor in the same manner as described above with respect to a 24-well plate with each of the well units 211, 212, 213, and 214, extending into a corresponding well of the multi-well plate of the bioreactor so that biological experimentation may be conducted. In this regard, the configuration and design of handling system 201 is advantageously configured to permit perfusion of cell culture media through the scaffolds. For example, the reliable and repeatable positioning of the carrier 205 is configured to hold the scaffold(s) 220 in the flow line of the perfusion bioreactor such that cell culture media flows through the scaffold from the distal end to the proximal end of each well unit 210. Overflow channel or opening 239 facilitates the return flow of perfusion media out though the proximal side of the scaffold 220.

Referring again to FIG. 17, an exemplary method of handling or manipulating a scaffold or scaffolds 220 according to the present invention is also shown. As shown with respect to well unit 211, as an initial step, a scaffold 220 or multiple scaffolds may be loaded or inserted into well units 210 of carrier 205. Once installed or loaded into carrier 205, as shown with respect to well unit 212, the scaffold(s) 220 may then be manipulated such as by being treated with chemicals, sterilized with ultraviolet radiation, seeded with cells, or other treatments. Similarly, as shown with respect to well unit 213, the scaffold may be inserted into a multi-well plate with cell culture media or biological agents to conduct biological experiments. As shown with respect to well unit 214 of FIG. 17, media can be perfused through scaffold(s) 220. Also, if microscopy is necessary, carrier 205 can be easily moved to a separate or fresh dry plate for microscopy without the need to handle the scaffolds directly.

EXAMPLE 1

Referring to FIG. 8, one example of a cell biology experiment performed according to the invention is shown wherein primary rat hepatocytes were seeded onto alginate scaffolds in the perfusion chamber, and cultured with Hepatostim media under perfusion flow. The same cells were also seeded onto matrigel substrates (typically known to maintain basal CYP 3A1 activity for rat hepatocytes), and passive coated collagen type 1 substrate were used as a negative control (typically known to decrease basal CYP 3A1 activity for rat hepatocytes). After 48 hours, 100 uM cortexolone was added to the media to induce CYP 3A1 expression. At weekly time points, the basal 3A1 activity was monitored by testosterone metabolism into 6B-hydroxytestosterone using HPLC analysis. The level of 6B-hydroxytestosterone in the culture is therefore indicative of CYP 3A1 expression and activity. The collagen cultures did not allow for CYP 3A1 expression, and the matrigel cultures helped the hepatocytes maintain CYP 3A1 expression for 3 weeks, at which point expression decreased. Hepatocytes cultured under fluid flow on aligned scaffolds also maintained elevated CYP 3A1 activity, but instead of decreasing at 4 weeks, the activity increased dramatically compared to the matrigel. This example demonstrates that cells may be grown in this device configuration and also suggests that the novel culture conditions allowed for extended and higher expression of differentiation-specific cell function for primary rat cells. Under perfusion flow, important p450 3A1 function is maintained for 4 weeks, longer than industry standard matrigel cultures.

EXAMPLE 2

Figure 14:
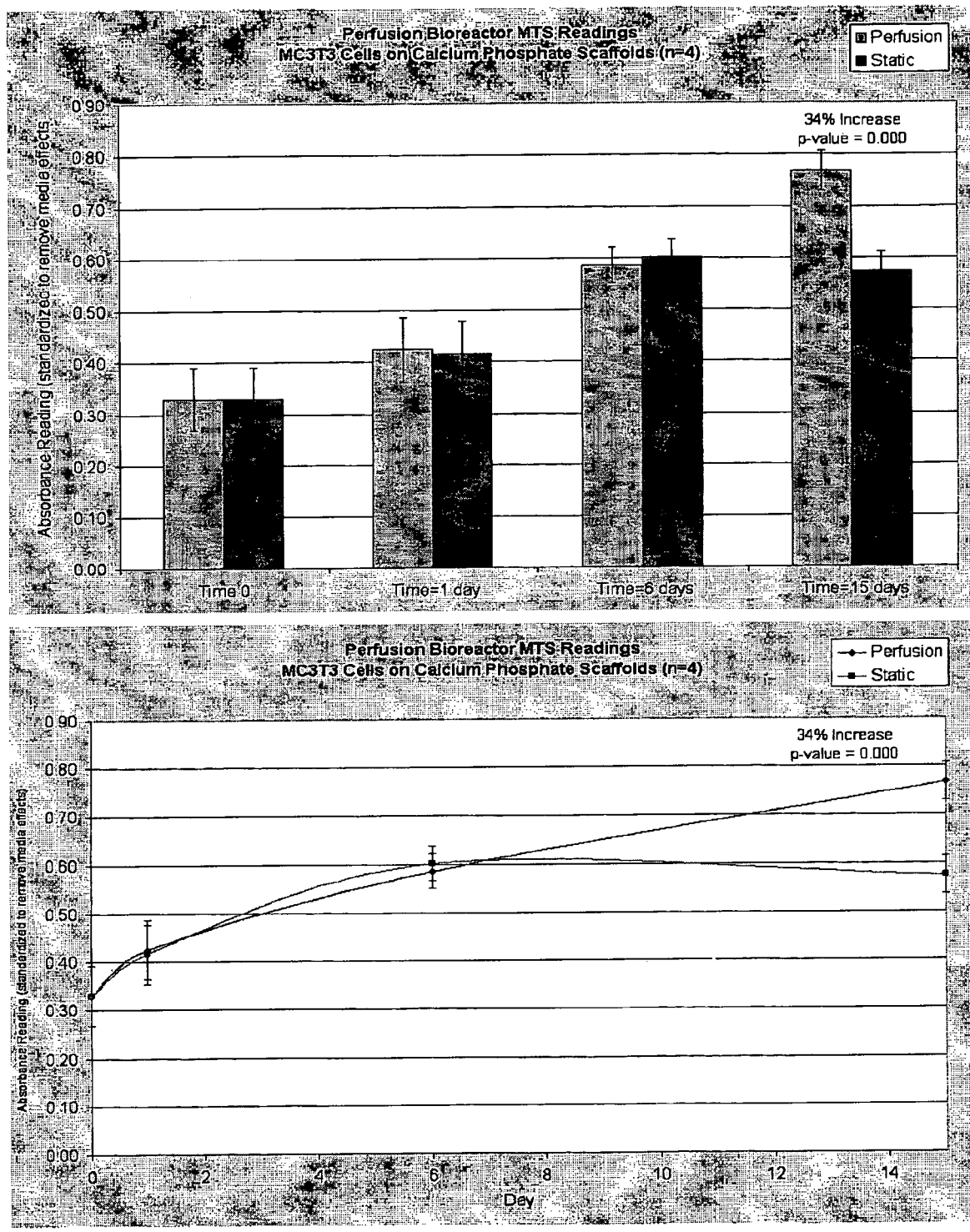
FIGS. 14-16 are graphical representations of additional examples of cell biology experiments performed according to the invention.

Referring to FIG. 14, one example of a cell biology experiment performed according to the invention is shown wherein mouse osteoblastic cells (MC3T3s) were seeded on calcium phosphate scaffolds, and cultured with Gibco Alpha media under perfusion flow. The same cells were also seeded on calcium phosphate scaffolds in a static condition. The metabolic activity of the cells was studied via absorbance under static and perfusion conditions for a period of 15 days. After 15 days, the cells under perfusion show a statistically significant increase of 34% in metabolic activity over the cells in the static condition.

EXAMPLE 3

Figure 15:
Figure 15:
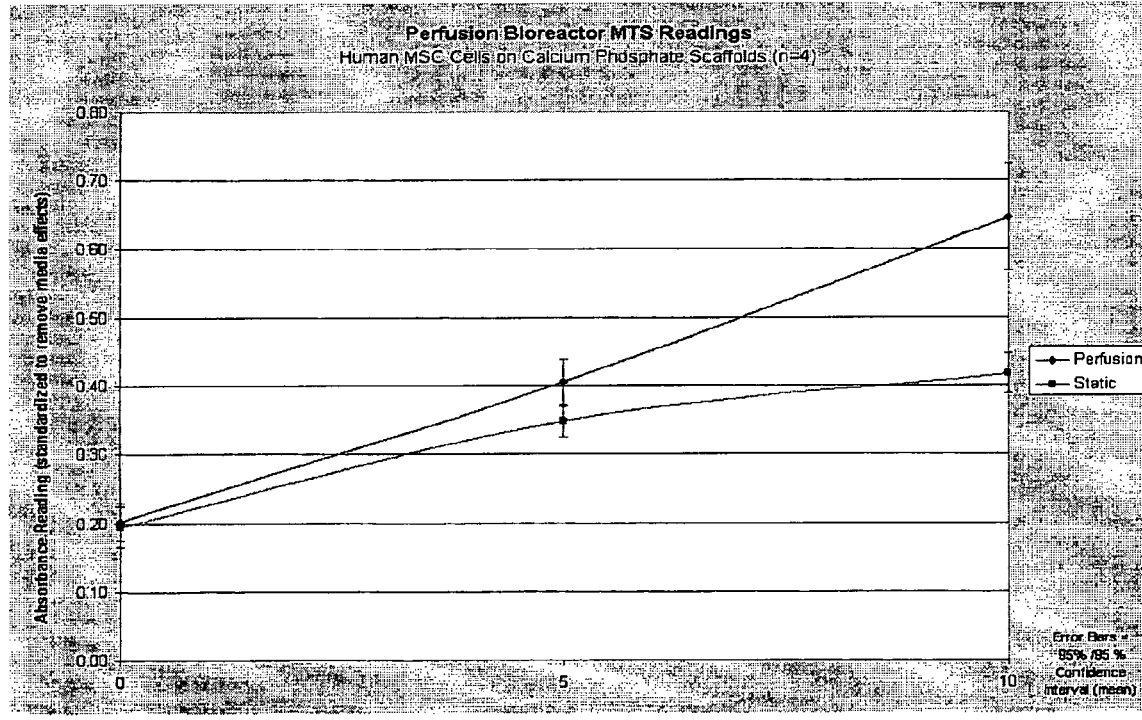

Referring to FIG. 15, one example of a cell biology experiment performed according to the invention is shown wherein human mesenchymal stem cells (MSCs) were seeded on calcium phosphate scaffolds, and cultured with Osteogenesis media under perfusion flow. The same cells were also seeded on calcium phosphate scaffolds in a static condition. The metabolic activity of the cells was studied via absorbance under static and perfusion conditions for a period of 10 days. After 10 days, the cells under perfusion show a statistically significant increase of 42% in metabolic activity over the cells in the static condition.

EXAMPLE 4

Figure 16:
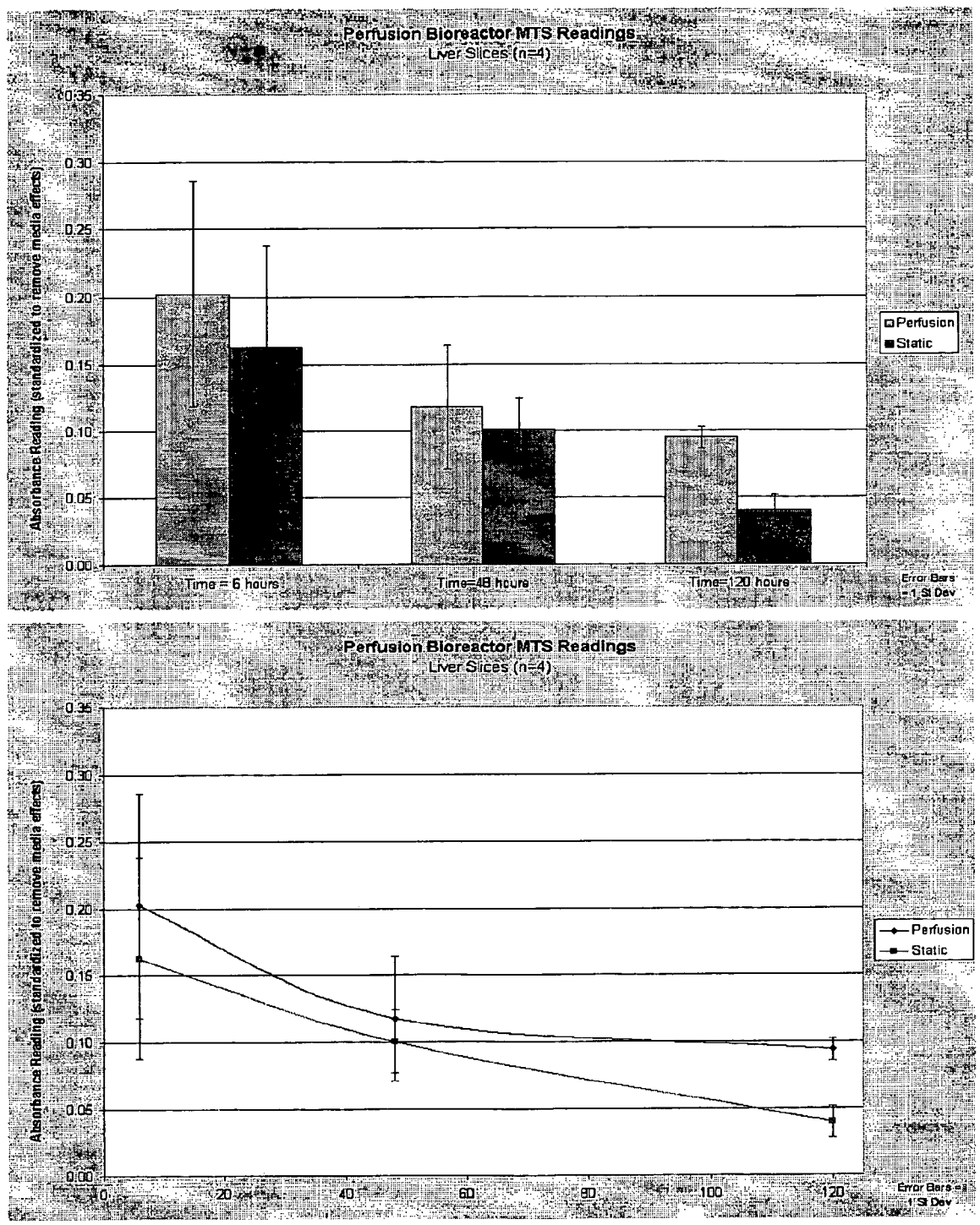

Referring to FIG. 16, one example of a cell biology experiment performed according to the invention is shown wherein rat liver slices were cultured with Gibco media under perfusion flow. The slices were also cultured in a static condition. The metabolic activity of the cells was studied via absorbance under static and perfusion conditions for a period of 5 days. After 5 days, the slices under perfusion show a statistically significant increase of 136% in metabolic activity over the slices in the static condition.

While the invention has been described in conjunction with specific embodiments and examples thereof, it is evident that many alternatives, modifications and variations will be apparent to those skilled in the art upon reading the present disclosure. Accordingly, it is intended to embrace all such alternatives, modifications and variations that fall within the spirit and broad scope of the appended claims.

What is claimed is:

1. A bioreactor system, comprising:
   a perfusion unit including an array of cell wells configured to contain cell cultures;
   a pumping unit comprising an array of pumping elements in fluid communication with said cell wells, wherein each pumping element comprises a fluid stem having a fluid port therein, and wherein each stem is adapted and configured to extend into the cell wells; and
   a discrete fluid source unit comprising an array of media wells configured to contain cell culture media, wherein said media wells are in fluid communication with said pumping elements, wherein the pumping elements are configured to pump cell culture media from the media wells to the cell wells, each media well being substantially axially aligned with its corresponding cell well.

2. The system of claim 1, wherein each of said cell wells is adapted and configured to contain a scaffold having a porous structure.

3. The system of claim 2, wherein each of said cell wells is adapted and configured to contain a two-dimensional scaffold.

4. The system of claim 2, wherein fluid is deliverable directly into the internal structure of said scaffold.

5. The system of claim 4, further comprising at least one return pathway for the fluid to flow from the array of cell wells to the array of media wells.

6. The system of claim 5, further comprising a plurality of return pathways and each return pathway is in fluid communication with a single cell well and a single media well.

7. The system of claim 1, wherein the perfusion unit is removably couplable to the pumping unit.

8. The system of claim 1, wherein each cell well includes a scaffold coupled thereto and configured to receive a portion of the stem internal thereto.

9. The system of claim 1, wherein the fluid source unit is removably couplable to the pumping unit.

10. The system of claim 1, wherein the pumping element comprises at least one one-way valve and is operable by air pressure.

11. The system of claim 1, further comprising a scaffold carrier cartridge comprising an array of well units wherein, a cell adherent scaffold may be positioned in each well unit, and wherein the cartridge is coupleable with the perfusion unit such that each well unit aligns with a cell well of the perfusion unit.

12. A plate for use in cell culture experiments, comprising:
    a plurality of chambers configured to contain cell cultures, each chamber having a base portion defining a fluid port having a first axis and being adapted to receive an outlet of a pump unit, the base portion further defining a fluid return pathway having a longitudinal axis substantially parallel to the first axis, each chamber further having a post structure extending from the base portion within the chamber and being spaced apart from the fluid port, the post structure being configured to support a cell specimen attached to the chamber about the fluid port.

13. The plate of claim 12, wherein the cell specimen comprises a cell adherent structure.

14. The plate of claim 12, wherein the cell culture is grown under fluid flow conditions.

15. The plate of claim 13, wherein the cell adherent structure is a two-dimensional scaffold.

* * * * *